(12) United States Patent
Hummer et al.

(10) Patent No.: US 12,600,636 B1
(45) Date of Patent: Apr. 14, 2026

(54) FUNCTIONALIZED GRAPHENE AND METHODS OF USE THEREOF

(71) Applicants: Matthew Hummer, Shaker Heights, OH (US); Gregory J. Hummer, Shaker Heights, OH (US)

(72) Inventors: Matthew Hummer, Shaker Heights, OH (US); Gregory J. Hummer, Shaker Heights, OH (US)

( * ) Notice: Subject to any disclaimer, the term of this patent is extended or adjusted under 35 U.S.C. 154(b) by 0 days.

(21) Appl. No.: 19/260,530

(22) Filed: Jul. 6, 2025

Related U.S. Application Data

(63) Continuation-in-part of application No. 16/926,702, filed on Jul. 11, 2020, now Pat. No. 11,172,339.

(51) Int. Cl.
| | |
|---|---|
| *C01B 32/194* | (2017.01) |
| *C09D 11/037* | (2014.01) |
| *G01N 33/50* | (2006.01) |

(52) U.S. Cl.
CPC .......... *C01B 32/194* (2017.08); *C09D 11/037* (2013.01); *G01N 33/50* (2013.01); *C01B 2204/32* (2013.01); *C01P 2002/82* (2013.01); *C01P 2006/10* (2013.01); *C01P 2006/12* (2013.01); *C01P 2006/22* (2013.01)

(58) Field of Classification Search
CPC . C01B 32/194; C01B 2204/32; C09D 11/037; G01N 33/50; C01P 2002/82; C01P 2006/10; C01P 2006/12; C01P 2006/22
See application file for complete search history.

(56) References Cited

PUBLICATIONS

Mansourian-Tabaei, Mohammad, et al. "Polyurea/aminopropyl isobutyl polyhedral oligomeric silsesquioxane-functionalized graphene nanoplatelet nanocomposites for force protection applications." ACS Applied Materials & Interfaces 16.15 (2024): 19625-19641.*
Jia, Yunfang, et al. "Graphene oxide modified light addressable potentiometric sensor and its application for ssDNA monitoring." Analyst 137.24 (2012): 5866-5873.*

(Continued)

*Primary Examiner* — Richard M Rump
(74) *Attorney, Agent, or Firm* — Edmond DeFrank

(57) ABSTRACT
A graphene-based composition is disclosed comprising functionalized graphene powder produced by detonation, plasma synthesis, liquid phase exfoliation, mechanical exfoliation among other graphene production methods known in the art. The graphene powder includes oxygen-containing functional groups such as hydroxyl, epoxy, carbonyl, and carboxyl, with a carbon-to-oxygen atomic ratio ranging from approximately 1.0 to 99.0. The powder is dispersed in an organic solvent, non-organic solvent, aqueous medium, surfactant, or POSS-based medium at a solids concentration between about 2% w/v and 30% w/v. Methods of functionalizing the graphene powder and forming dispersions are provided, along with methods of making ink dispersions with polymer binders and printed or coated articles formed therefrom. The graphene formulations exhibit tunable surface chemistry, controlled defect structures as measured by Raman spectroscopy, and stable dispersion properties suitable for applications in printed electronics, conductive coatings, sensing platforms, and lightweight composites.

10 Claims, 21 Drawing Sheets

(56) References Cited

PUBLICATIONS

Smith, Emily AM, et al. "Plasma functionalisation of few-layer graphenes and carbon nanotubes for graphene microsupercapacitors." Electrochimica Acta 317 (2019): 348-357.*

Cunha, Eunice, and Maria C. Paiva. "Composite films of water-borne polyurethane and few-layer graphene-enhancing barrier, mechanical, and electrical properties." Journal of Composites Science 3.2 (2019): 35.*

Hong, Bong Jin, et al. "Tunable biomolecular interaction and fluorescence quenching ability of graphene oxide: Application to "turn-on" DNA sensing in biological media." Small (Weinheim an der Bergstrasse, Germany) 8.16 (2012): 2469.*

* cited by examiner

Surface Chemistry (C/O = 1.50) — 1000

| REQUIREMENT/ TOLERANCE | C 1s (At%) | O 1s (At%) | C/O ratio | C=C (At%) | C-OH / C-O-C (At%) | C=O (At%) | O-C=O (At%) |
|---|---|---|---|---|---|---|---|
| 1002 / 1004 | 1010 | 1012 | 1014 | 1016 | 1018 | 1020 | 1022 |
| REQUIREMENT | 60.00 | 40.00 | 1.50 | 46.08 | 8.46 | 2.40 | 3.06 |
| TOLERANCE | 10.00 | 10.00 | 11.09 | 1.50 | 0.80 | 0.60 | 0.10 |

1006

Raman Structural Ratios (C/O = 1.50) — 1040

| REQUIREMENT/ TOLERANCE | AD/AG | AD'/AG | A2D/AG | AD/AD' |
|---|---|---|---|---|
| 1002 / 1004 | 1030 | 1032 | 1034 | 1036 |
| REQUIREMENT | 6.89 | 0.83 | 0.10 | 0.99 |
| TOLERANCE | 0.50 | 0.20 | 0.02 | 0.50 |

1006

Surface Chemistry (C/O = 4.00) 1100

| REQUIREMENT/TOLERANCE | C 1s (At%) | O 1s (At%) | C/O ratio | C=C (At%) | C-OH / C-O-C (At%) | C=O (At%) | O-C=O (At%) |
|---|---|---|---|---|---|---|---|
| | 1010 | 1012 | 1014 | 1016 | 1018 | 1020 | 1022 |
| REQUIREMENT | 80.00 | 20.00 | 4.00 | 61.44 | 11.28 | 3.20 | 4.08 |
| TOLERANCE | ±10.00 | ±10.00 | ±11.09 | ±1.50 | ±0.80 | ±0.60 | ±0.10 |

Raman Structural Ratios (C/O = 4.00) 1110

| REQUIREMENT/TOLERANCE | AD/AG | AD'/AG | A2D/AG | AD/AD' |
|---|---|---|---|---|
| | 1030 | 1032 | 1034 | 1036 |
| REQUIREMENT | 2.59 | 0.31 | 0.26 | 2.64 |
| TOLERANCE | 0.25 | 0.10 | 0.06 | 1.00 |

Surface Chemistry (C/O = 19.00) — 1200

| REQUIREMENT/ TOLERANCE | C 1s (At%) 1010 | O 1s (At%) 1012 | C/O ratio 1014 | C=C (At%) 1016 | C-OH / C-O-C (At%) 1018 | C=O (At%) 1020 | O-C=O (At%) 1022 |
|---|---|---|---|---|---|---|---|
| REQUIREMENT | 95.00 | 5.00 | 19.00 | 72.96 | 13.40 | 3.80 | 4.85 |
| TOLERANCE | ±5.00 | ±5.00 | ±11.40 | ±1.50 | ±0.80 | ±0.60 | ±0.10 |

1002  1004     1006

Raman Structural Ratios (C/O = 19.00) — 1210

| REQUIREMENT/ TOLERANCE | AD/AG 1030 | AD'/AG 1032 | A2D/AG 1034 | AD/AD' 1036 |
|---|---|---|---|---|
| REQUIREMENT | 0.54 | 0.07 | 1.21 | 12.56 |
| TOLERANCE | 0.03 | 0.02 | 0.10 | 3.15 |

1002  1004     1006

| REQUIREMENT/ TOLERANCE | C 1s (At%) | O 1s (At%) | C/O ratio | C=C (At%) | C-OH / C-O-C (At%) | C=O (At%) | O-C=O (At%) |
|---|---|---|---|---|---|---|---|
| REQUIREMENT | 99.00 | 1.00 | 99.00 | 76.03 | 13.93 | 3.96 | 5.05 |
| TOLERANCE | ±2.00 | ±2.00 | ±1.09 | ±1.50 | ±0.80 | ±0.60 | ±0.10 |

Surface Chemistry (C/O = 99.00) — 1300

| REQUIREMENT/ TOLERANCE | AD/AG | AD'/AG | A2D/AG | AD/AD' |
|---|---|---|---|---|
| REQUIREMENT | 0.03 | 0.005 | 2.5 | — |
| TOLERANCE | 0.01 | 0.005 | 0.5 | — |

Raman Structural Ratios (C/O = 99.00) — 1310

1

FUNCTIONALIZED GRAPHENE AND METHODS OF USE THEREOF

CROSS-REFERENCE TO RELATED APPLICATIONS

This patent application is a Continuation-in-part and claims priority to the United States patent application entitled: "GRAPHENE INK COMPOSITION AND METHODS OF USE THEREOF", U.S. Ser. No. 18/928,124 filed on Oct. 27, 2024 by Matthew Hummer, which is a Continuation-in-part of United States patent application entitled: "DEVICE FOR READING, PROCESSING AND TRANSMITTING TEST RESULT DATA FOR PATHOGENS OR VIRUSES IN FLUID TEST SAMPLES", U.S. Ser. No. 18/896,643 filed on Sep. 25, 2024 by Matthew Hummer, which is a Continuation-in-part of United States patent application entitled: "DEVICE FOR READING, PROCESSING AND TRANSMITTING TEST RESULT DATA FOR PATHOGENS OR VIRUSES IN FLUID TEST SAMPLES ", U.S. Ser. No. 18/440,925 filed on Feb. 13, 2024 by Matthew Hummer, which is a continuation of United States Patent App Continuation-in-part application entitled: "DEVICE FOR READING, PROCESSING AND TRANSMITTING TEST RESULT DATA FOR PATHOGENS OR VIRUSES IN FLUID TEST SAMPLES", U.S. Ser. No. 17/505,611 filed on Oct. 19, 2021 by Matthew Hummer, which is a continuation-in-part of application entitled: "METHOD AND DEVICES FOR DETECTING VIRUSES AND BACTERIAL PATHOGENS", U.S. Ser. No. 17/324,085 filed on Jul. 11, 2020 by Matthew Hummer, which is a continuation-in-part and claims priority to the United States Patent Application entitled: "METHOD AND DEVICES FOR DETECTING CHEMICAL COMPOSITIONS AND BIOLOGICAL PATHOGENS", U.S. Ser. No. 16/926,701 filed on Jul. 11, 2020 by Gregory J. Hummer, the U.S. Patent Applications being incorporated herein by reference and which is a continuation-in-part and claims priority to the United States Patent Application entitled: "METHOD AND DEVICES FOR DETECTING CHEMICAL COMPOSITIONS AND BIOLOGICAL PATHOGENS", U.S. Ser. No. 16/926,702 filed on Jul. 11, 2020 by Gregory J. Hummer, the U.S. Patent Application being incorporated herein by reference, which is a continuation-in-part and claims priority to the United States Patent Application entitled: "MONITORING SYSTEM FOR USE WITH MOBILE COMMUNICATION DEVICE", U.S. Ser. No. 16/513,753 filed on Jul. 17, 2019 by Gregory J. Hummer, which is a continuation of and claims priority to the United States Patent Application entitled: 'MONITORING SYSTEM FOR USE WITH MOBILE COMMUNICATION DEVICE", U.S. Ser. No. 15/891,410 filed on Feb. 8, 2018 by Gregory J. Hummer, which is a continuation of and claims priority to the United States Patent Application entitled: "MONITORING SYSTEM FOR USE WITH MOBILE COMMUNICATION DEVICE", U.S. Ser. No. 15/235,981 filed on Aug. 12, 2016 by Gregory J. Hummer, which claims benefit of provisional United States Provisional Patent Application U.S. Ser. No. 62/297,385 filed on Feb. 19, 2016 by Gregory J. Hummer, which claims benefit of provisional United States Provisional Patent Application U.S. Ser. No. 62/205,012 filed on Aug. 14, 2015 by Gregory J. Hummer, all the U.S. Patent Applications being incorporated herein by reference.

BACKGROUND OF THE INVENTION

Functionalized graphene has emerged as a critical material for printed electronics, coatings, and advanced composites due to its high conductivity, tunable surface chemistry, and mechanical strength. However, scalable production of graphene powders with controlled oxygen-containing functional groups, dispersibility in multiple solvent systems, and reproducible structural properties remains a challenge.

Existing graphene production methods often lack the ability to simultaneously control the degree of oxidation, structural disorder, and dispersion stability. Moreover, conventional functionalization techniques frequently disrupt the graphene lattice, resulting in diminished electronic performance or inconsistent flake morphology. Additionally, there is limited understanding of how electrokinetic properties such as zeta potential relate to graphene's surface area, crystallinity, and defect state, which are essential for ink formulation and device reliability.

There remains a need for a composition and method that enables the production of functionalized graphene powder with tunable carbon-to-oxygen atomic ratios, controlled Raman and surface properties, and dispersion stability across aqueous and organic systems. The present invention addresses these challenges by providing a system and method for producing, characterizing, and dispersing functionalized graphene powder optimized for printability, substrate adhesion, and electrical performance.

SUMMARY OF THE INVENTION

The present invention provides compositions, methods and articles based on functionalized graphene powder characterized by controlled oxygen functionalization, dispersibility, and structural uniformity.

In one embodiment, the invention provides a composition comprising functionalized graphene powder dispersed in at least one solvent system and embedded within at least one polymer matrix. The composition may further include additives such as dispersing agents, wetting agents/surface tension modifiers, rheology modifiers/thickeners, binders/film formers, adhesion promoters, crosslinkers/curing agents, humectants/solvent retention aids, antifoaming agents, and pH buffers. The graphene powder includes oxygen-containing functional groups such as hydroxyl, epoxy, ether, carbonyl, carboxyl and ester, and is defined by a carbon-to-oxygen atomic ratio ranging from about 1.0 to about 99.0. The powder is dispersed in solvents selected from water, organic, inorganic, surfactant-based, or POSS-based systems at a solids concentration between about 2% and 30% w/v. The composition may further include polymers such as polyurethane (PU), polyacrylate/acrylics, epoxy, polyvinyl alcohol (PVA), polyvinylpyrrolidone (PVP), polyethylene glycol (PEG), polyimide precursors and cellulose derivatives (e.g. hydroxypropyl cellulose (HPC), carboxymethyl cellulose (CMC), hydroxyethyl cellulose (HEC) and ethyl cellulose) for forming printable or sprayable conductive composites.

The invention also provides methods for producing such functionalized graphene powder using exfoliation and activation techniques including plasma synthesis, detonation, sonication, milling, chemical vapor deposition (CVD), exfoliation, cavitation and other production methods. Functionalization may involve plasma oxidation, wet chemistry, POSS grafting, or silanization. Dispersion properties, crystallinity, and defect structure are monitored using Raman spectroscopy, zeta potential analysis and other characterization techniques included in this disclosure.

In certain embodiments, zeta potential is shown to correlate with specific surface area, crystallinity, flake orientation, and Raman band ratios, enabling predictive control over printability, dispersion stability, conductivity and substrate adhesion. The invention further provides dispersions suitable for various deposition methods and printed articles retaining conductivity and surface functionality post-deposition.

DETAILED DESCRIPTION OF THE INVENTION

Figure 1:
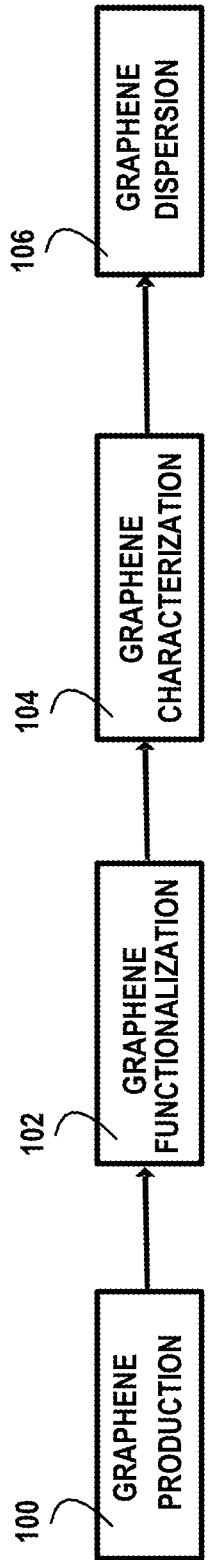
FIG. 1 shows a block diagram of an overview flow chart of sequential stages of graphene production, functionalization, characterization, and dispersion of one embodiment.

FIG. 1 shows a block diagram of an overview flow chart of sequential stages of graphene production, functionalization, characterization, and dispersion of one embodiment. FIG. 1 is a high-level of the sequential stages of graphene production 100, functionalization, characterization, and dispersion.

With reference to FIG. 1, an exemplary process for producing and preparing functionalized graphene materials is shown, comprising four major stages: graphene production 100, graphene functionalization 102, graphene characterization 104, and graphene dispersion 106. Each stage includes one or more methods described in greater detail in FIGS. 2-5.

The process begins with graphene production 100, which may include detonation-based synthesis, plasma methods, liquid exfoliation, mechanical exfoliation, and other production techniques such as chemical vapor deposition, pyrolysis, cavitation or high-shear processing. These methods generate graphene nanoflakes with controlled size distributions (25-3,000 nm), layer thicknesses (single to multilayer), and oxygen-containing surface functionalities (e.g., hydroxyl, epoxy, carbonyl, carboxyl), which enhance dispersion and reactivity.

Next, the material undergoes graphene functionalization 102, which modifies the surface chemistry using approaches such as covalent attachment, non-covalent adsorption, silanization, POSS-based grafting, plasma activation, or chemical treatment. These techniques enable improved dispersion, chemical compatibility, and application-specific surface reactivity.

Following modification, graphene characterization 104 is conducted using a suite of techniques. Chemical composition, structural properties, rheological behavior, thickness, electrical performance, and optical properties are evaluated to confirm material uniformity and application readiness.

Finally, the graphene material is subjected to dispersion 106 using selected solvent systems such as organic solvents, non-organic/polar solvents, surfactants, POSS derivatives, silane agents, or aqueous mediums 550. Dispersion techniques include temperature-controlled ultrasonication, high-shear mixing, and degassing, with dispersion quality verified by zeta potential (>+10-30 mV) and particle size uniformity.

Figure 2:
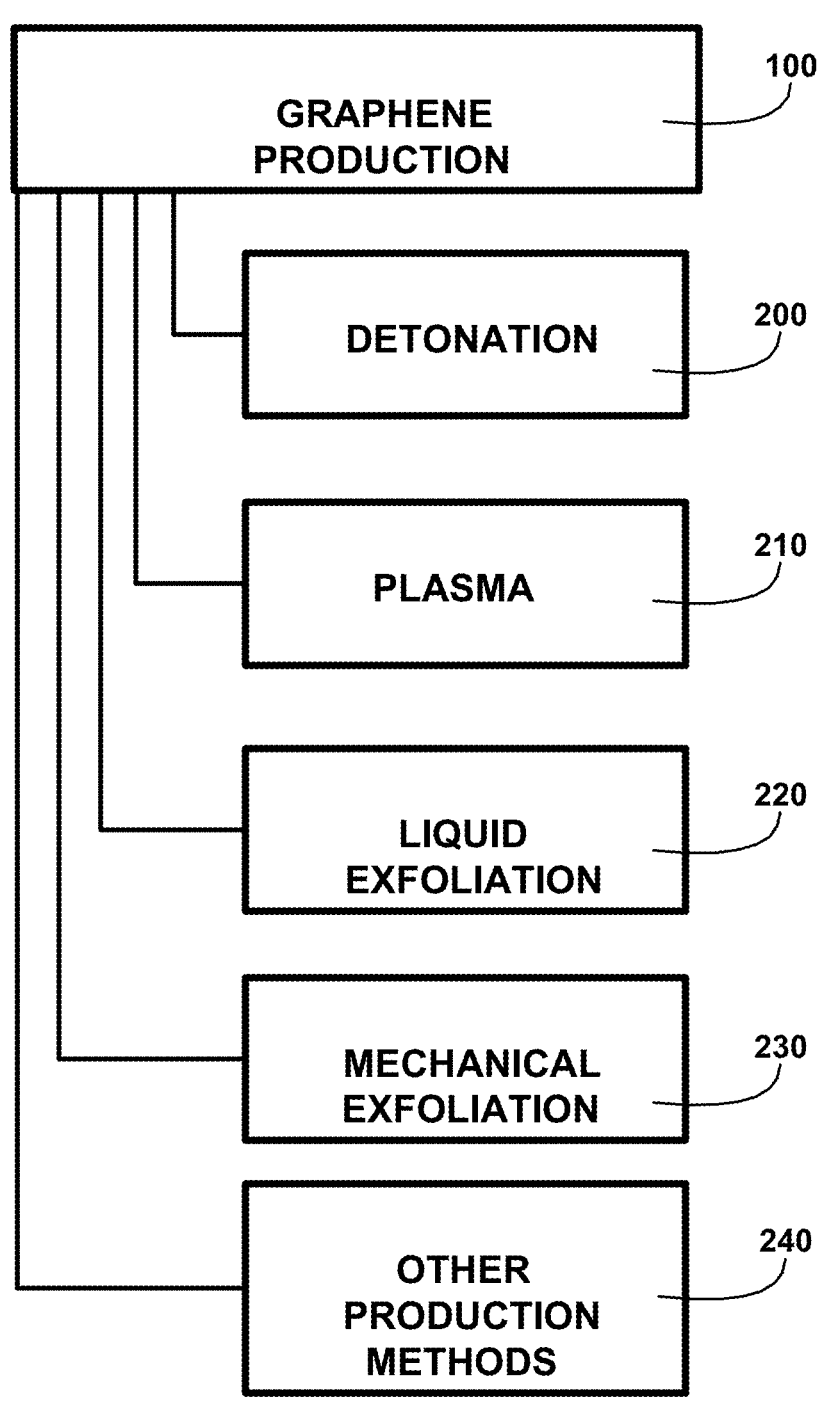
FIG. 2 shows a block diagram of an overview of graphene production methods of one embodiment.

FIG. 2 shows a block diagram of an overview of graphene production methods of one embodiment. FIG. 2 shows a hierarchical diagram of the categories of graphene production 100 methods, including detonation 200, plasma 210, liquid exfoliation 220, mechanical exfoliation 230, and other production methods 240.

With reference to FIG. 2, exemplary graphene production 100 methods include a range of scalable and controllable techniques suitable for generating high-quality graphene nanoflakes. These methods comprise detonation-based synthesis using controlled carbon precursors and post-detonation purification, and plasma 210 production, which involves ionized gas environments to form graphene sheets under thermal and pressure control. Liquid exfoliation 220 methods utilize sonication, shear, or solvent interactions to exfoliate graphite in polar media. Mechanical exfoliation 230 includes milling, abrasion, or cleavage-based techniques using selected graphite precursors. Additional other production methods 240 include chemical exfoliation, electrochemical synthesis, chemical vapor deposition (CVD), pyrolysis, cavitation, and other techniques known in the art. These processes yield graphene with controlled lateral sizes (25-3,000 nm), variable thickness (single-layer to multilayer), and inherent surface functional groups such as hydroxyl, epoxy, ether carbonyl, carboxyl and ester, which improve dispersibility and chemical compatibility in subsequent processing stages.

Figure 3:
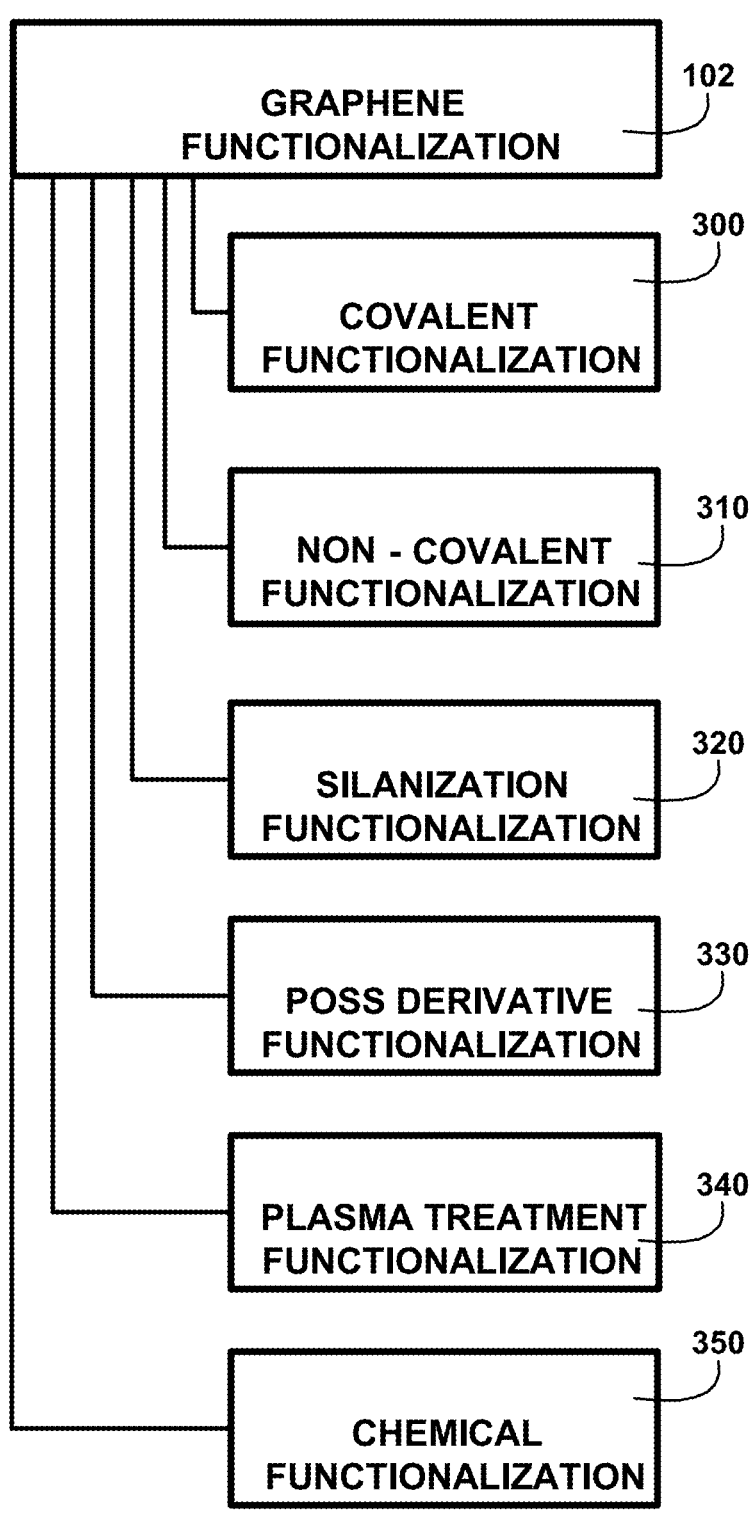
FIG. 3 shows a block diagram of an overview of different categories of graphene functionalization of one embodiment.

FIG. 3 shows a block diagram of an overview of different categories of graphene functionalization of one embodiment. FIG. 3 is a hierarchical diagram showing different categories of graphene functionalization 102, including covalent functionalization 300, non-covalent functionalization 310, silanization functionalization 320, POSS derivative functionalization 330, plasma treatment functionalization 340, and chemical functionalization 350 methods. With reference to FIG. 3, exemplary graphene functionalization 102 methods are illustrated, encompassing a range of surface modification techniques used to tailor the chemical and physical properties of graphene materials. These methods include covalent functionalization 300, in which reactive chemical groups are bonded directly to the graphene lattice at defect or edge sites to enable robust molecular attachment. Non-covalent functionalization 310 leverages IT-IT interactions, van der Waals forces, or hydrophobic effects to adsorb functional molecules without disrupting the $sp^2$ carbon structure. Silanization functionalization 320 uses organosilanes to form molecular bridges between the graphene surface and reactive groups, enhancing hydrophilicity and binding capacity. POSS derivative functionalization 330 involves silanization functionalization 320 grafting polyhedral oligomeric silsesquioxanes onto the graphene surface to improve steric stability and provide reactive moieties for downstream biofunctionalization. Plasma treatment functionalization 340 introduces oxygen-containing functional groups via ionized gas exposure, enabling surface activation without the use of solvents. Lastly, chemical functionalization 350 employs solution-phase reactions to covalently introduce targeted functional groups for dispersion, sensing, or integration with composite systems. Each functionalization approach offers distinct advantages depending on the intended application and desired surface chemistry.

Figure 4:
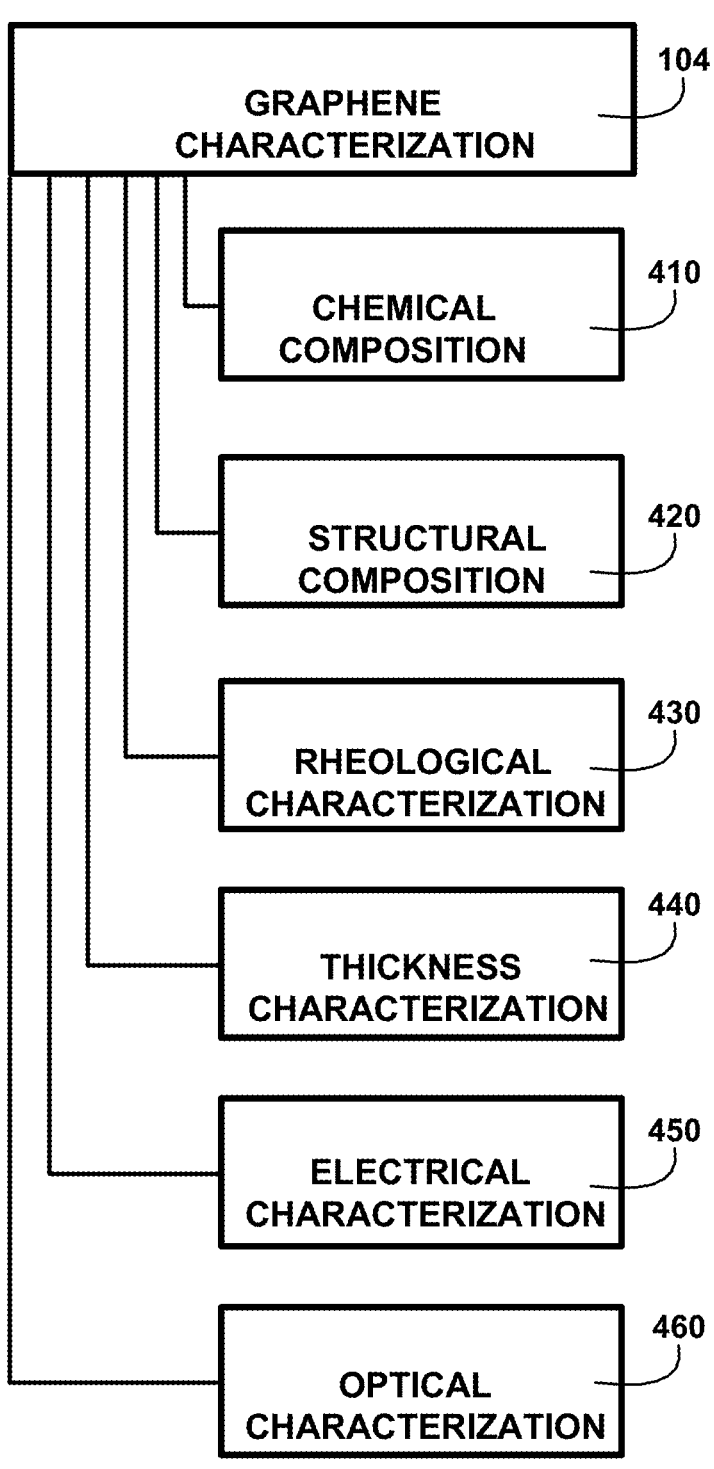
FIG. 4 shows a block diagram of an overview of a hierarchical diagram categorizing graphene characterization domains of one embodiment.

FIG. 4 shows a block diagram of an overview of a hierarchical diagram categorizing graphene characterization domains of one embodiment. FIG. 4 shows a hierarchical diagram categorizing graphene characterization 104 domains, including chemical composition 410, structural composition 420, rheological characterization 430, thickness characterization 440, electrical characterization 450, and optical characterization 460.

With reference to FIG. 4, exemplary graphene characterization 104 techniques are illustrated for assessing the quality, uniformity, and functional readiness of graphene materials following production and functionalization. These include chemical composition 410 analysis, which determines the elemental makeup and functional group distribution using techniques such as X-ray photoelectron spectroscopy (XPS), Fourier-transform infrared spectroscopy (FTIR), and X-ray diffraction (XRD). Structural composition 420 characterization includes Raman spectroscopy, transmission electron microscopy (TEM), and scanning electron microscopy (SEM) to evaluate morphology, crystallinity, layer number, and defect density. Rheological characterization 430 assesses flow behavior and viscosity of graphene dispersions 106 using shear rheometry and viscometry, critical for ink and formulation consistency. Thickness characterization 440 measures layer thickness and film uniformity using atomic force microscopy (AFM) and ellipsometry. Electrical characterization 450 evaluates conductivity, sheet resistance, and electronic uniformity using four-point probe methods, conductive AFM (C-AFM), and scanning Kelvin probe microscopy (SKPM). Optical characterization 460 includes measurements of light absorption, transmission, and photoluminescence using UV-Vis-NIR spectroscopy and ellipsometry. These methods provide comprehensive data for quality assurance and application-specific optimization.

Figure 5:
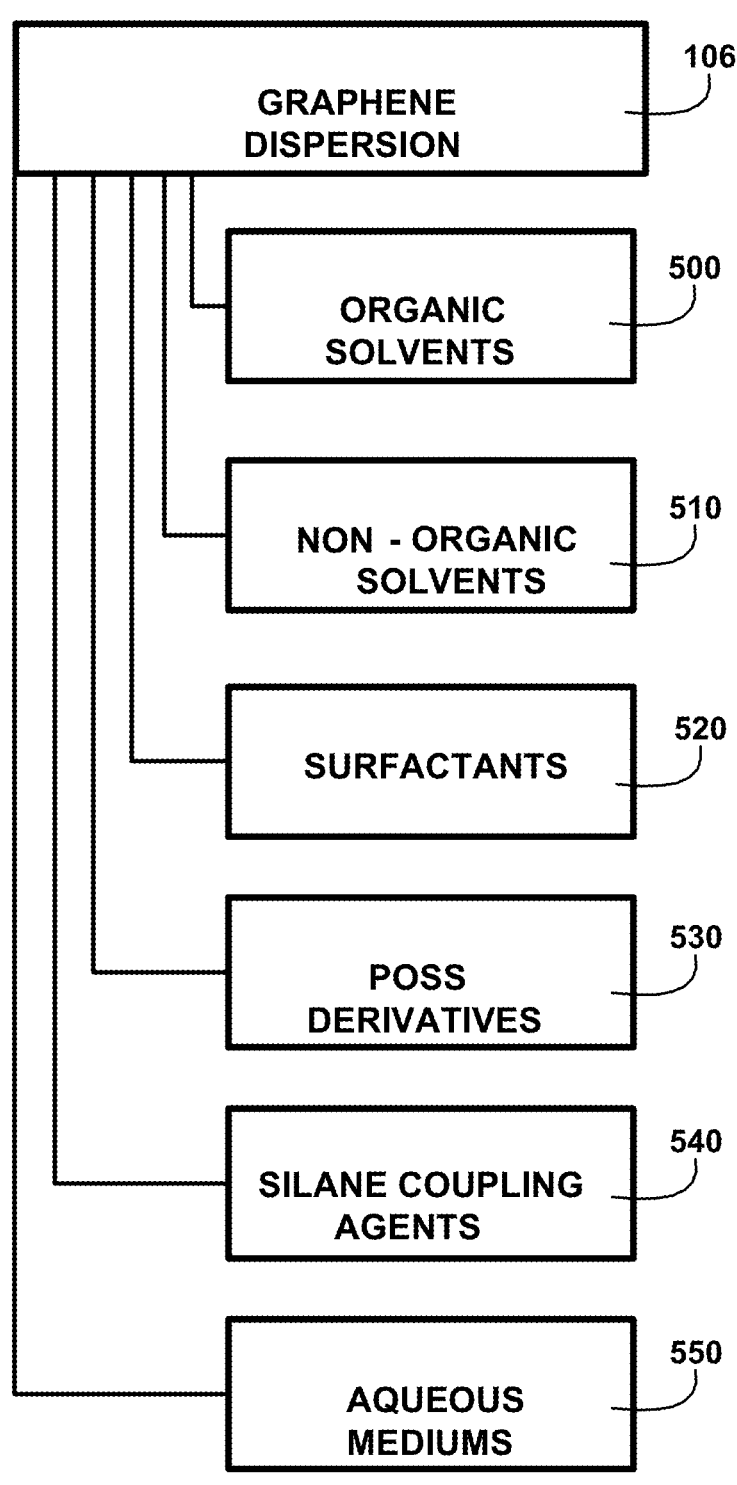
FIG. 5 shows a block diagram of an overview of a hierarchical diagram outlining categories of graphene dispersion systems of one embodiment.

FIG. 5 shows a block diagram of an overview of a hierarchical diagram outlining categories of graphene dispersion systems of one embodiment. FIG. 5 is a hierarchical diagram outlining categories of graphene dispersion 106 systems using organic solvents 500, non-organic solvents 510, surfactants 520, POSS derivatives 530, silane coupling agents 540, and aqueous media 550. With reference to FIG. 5, exemplary methods for graphene dispersion 106 are illustrated, showing various classes of dispersion agents used to stabilize graphene nanoflakes in liquid media. These include organic solvents 500 such as N-methyl-2-pyrrolidone (NMP), dimethylformamide (DMF), tetrahydrofuran (THF), terpene alcohols, butanol, ethanol selected for favorable surface energy matching with graphene. Non-organic solvents 510 encompass polar inorganic solvents 922 of FIG. 9A and ionic liquids 912 of FIG. 9A, which can promote stable dispersion without introducing organic impurities.

Figure 9A:
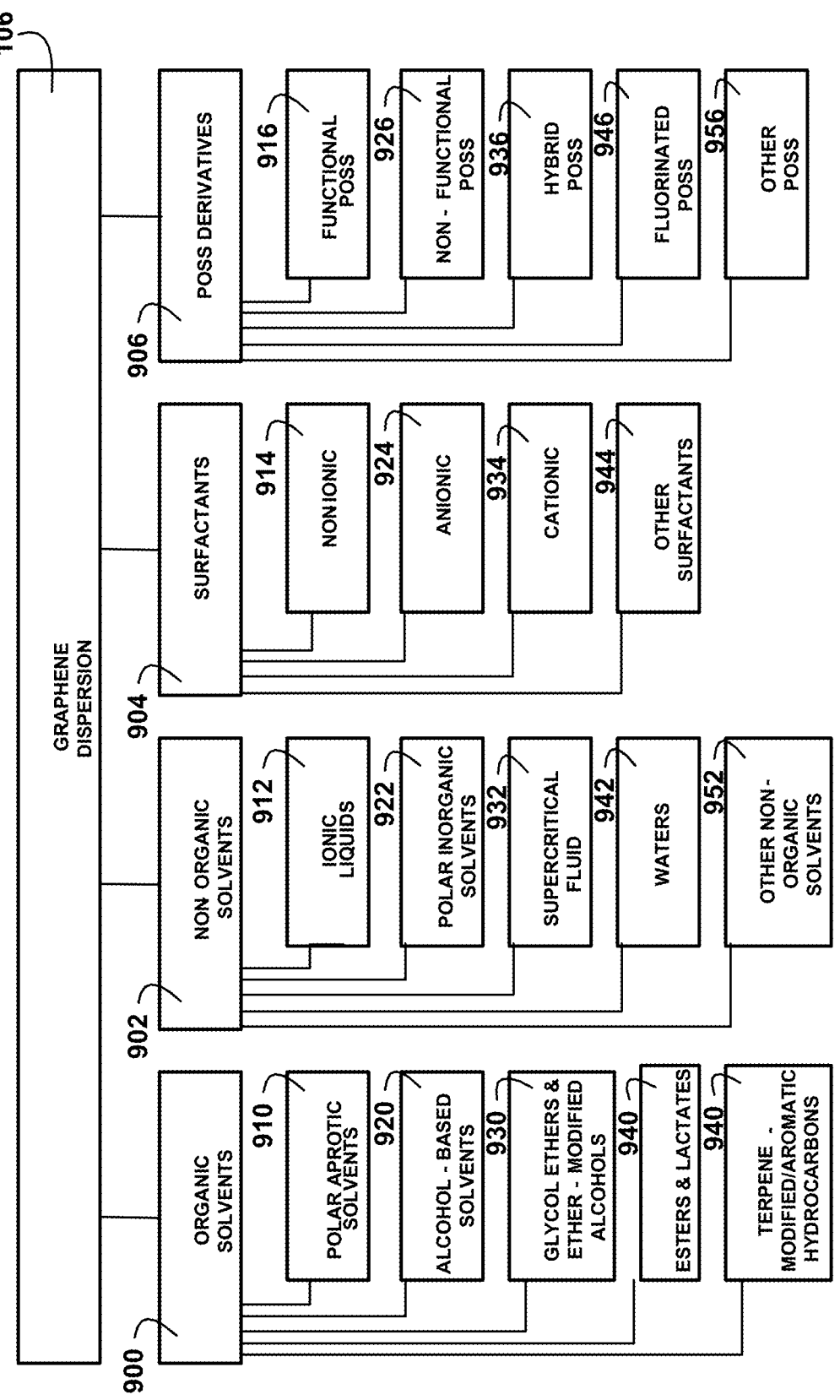
FIG. 9A shows a block diagram of an overview of a hierarchical diagram organizing graphene dispersion components of one embodiment.

Surfactants 520, including anionic 924 of FIG. 9A (e.g., SDS, SDBS), cationic 934 of FIG. 9A, and non-ionic species (e.g., Triton X-100), are employed to provide steric and electrostatic stabilization around dispersed graphene flakes. POSS derivatives 530 serve as cage-like nanostructured additives that sterically stabilize graphene dispersions 106 through surface adsorption and chemical compatibility. Silane coupling agents 540 are used to create chemical bridges between the graphene surface and solvent environment following plasma or chemical activation of the graphene. Lastly, aqueous mediums 550, including deionized water or buffered solutions, are employed in green formulations using dual-frequency ultrasonication, temperature control, and degassing to create stable, sedimentation-free graphene suspensions with zeta potential exceeding ±30 mV. Each of these dispersion systems enhances colloidal stability, prevents agglomeration, and enables downstream formulation for printing, coating, or biological applications.

Figure 6A:
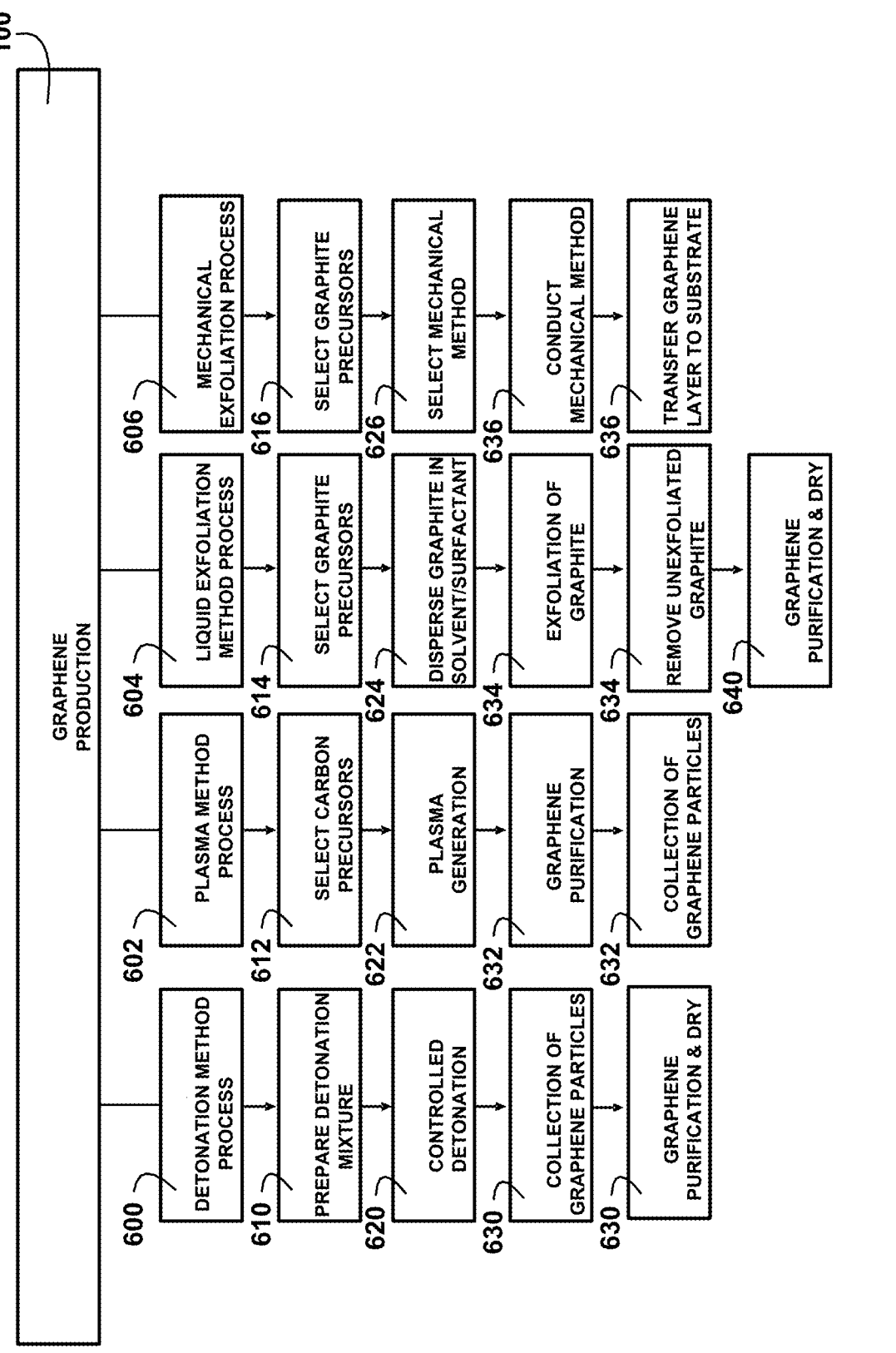
FIG. 6A shows a block diagram of an overview flow chart of stepwise processes for graphene production of one embodiment.

FIG. 6A shows a block diagram of an overview flow chart of stepwise processes for graphene production of one embodiment. FIG. 6A shows a flow diagram illustrating stepwise processes for graphene production 100 by detonation method process 600, plasma method process 602 synthesis, liquid exfoliation method process 604, and mechanical exfoliation method process 606. With reference to FIG. 6, exemplary graphene production 100 methods are illustrated. These methods are designed to produce high-purity graphene materials at scale, with controlled layer number, defect density, and surface chemistry. The four primary production pathways shown include detonation method process 600, plasma method process 602 synthesis, liquid exfoliation method process 604, and mechanical exfoliation method process 606, each with method-specific steps and purification protocols.

In one embodiment, the detonation method process 600 begins with preparing a detonation mixture 610 consisting of select carbon precursors 612 and oxidizers. Controlled detonation 620 initiates high-energy shockwave decomposition, forming few-layer graphene particles. The resulting collection of graphene particles 630 and subjected to graphene purification and drying 640 to remove residual metals and amorphous carbon. In a particular embodiment, a staged cooling system is incorporated downstream of the detonation chamber to minimize graphene agglomeration during recovery, improving material yield and dispersion quality.

In another embodiment, the plasma method process 602 begins with select carbon precursors 612, such as methane, acetylene, or carbon monoxide gases. These gases are introduced into a plasma chamber under reduced pressure. Plasma generation 622 induces fragmentation and reassembly of carbon species to form graphene. The product is subjected to plasma-assisted graphene purification 632, in which in situ reactive species remove amorphous carbon during the growth and recovery phase. The purified graphene is processed into a collection of graphene particles 642 via filtration or inert gas flow capture.

In a further embodiment, the liquid exfoliation method process 604 starts with select graphite precursors 614, which are processed to disperse graphite in a solvent or surfactant 624 containing solution. Exfoliation of graphite 634 is achieved using ultrasonication or high-shear mixing, delaminating graphite into mono- and few-layer graphene sheets. Unexfoliated graphite is removed 644 by centrifugation or membrane filtration, followed by graphene purification and drying 646 of the dispersion. In one preferred embodiment, a sequential centrifugation protocol is employed to isolate monolayer, bilayer, and few-layer fractions based on sedimentation behavior, improving dispersion consistency and application performance.

In another embodiment, the mechanical exfoliation process 606 involves select graphite precursors 616 and applying select mechanical method 626 forces, such as ball milling, shear blending, or roller compression. These forces are used to conduct mechanical exfoliation method 636 of the graphite structure. The resulting graphene material is configured as a graphene layer and may be transferred to a substrate 646 or collected as a powder. In a preferred embodiment, exfoliation is conducted at sub-ambient temperatures to reduce thermal degradation and defect formation, preserving electrical and mechanical properties.

In addition to the methods shown in FIG. 6A, other applicable graphene production 100 techniques include mechanical cleavage, chemical exfoliation, electrochemical processes, thermal exfoliation, milling, high shear mixing, sonication, chemical vapor deposition (CVD), separation/filtration, pyrolysis, and cavitation. These techniques may be applied individually or in combination to generate graphene materials with tailored lateral dimensions, thickness, and surface functionality.

All graphene production 100 methods are followed by a graphene purification and drying step 646, which may include solvent washing, vacuum drying, and thermal annealing under ambient or inert gas atmospheres to remove adsorbed species and ensure material consistency. In some embodiments, a wet transfer process is employed post-synthesis to relocate the exfoliated graphene to target substrates, enabling seamless integration into electronic devices, sensors, or barrier films.

Figure 6B:
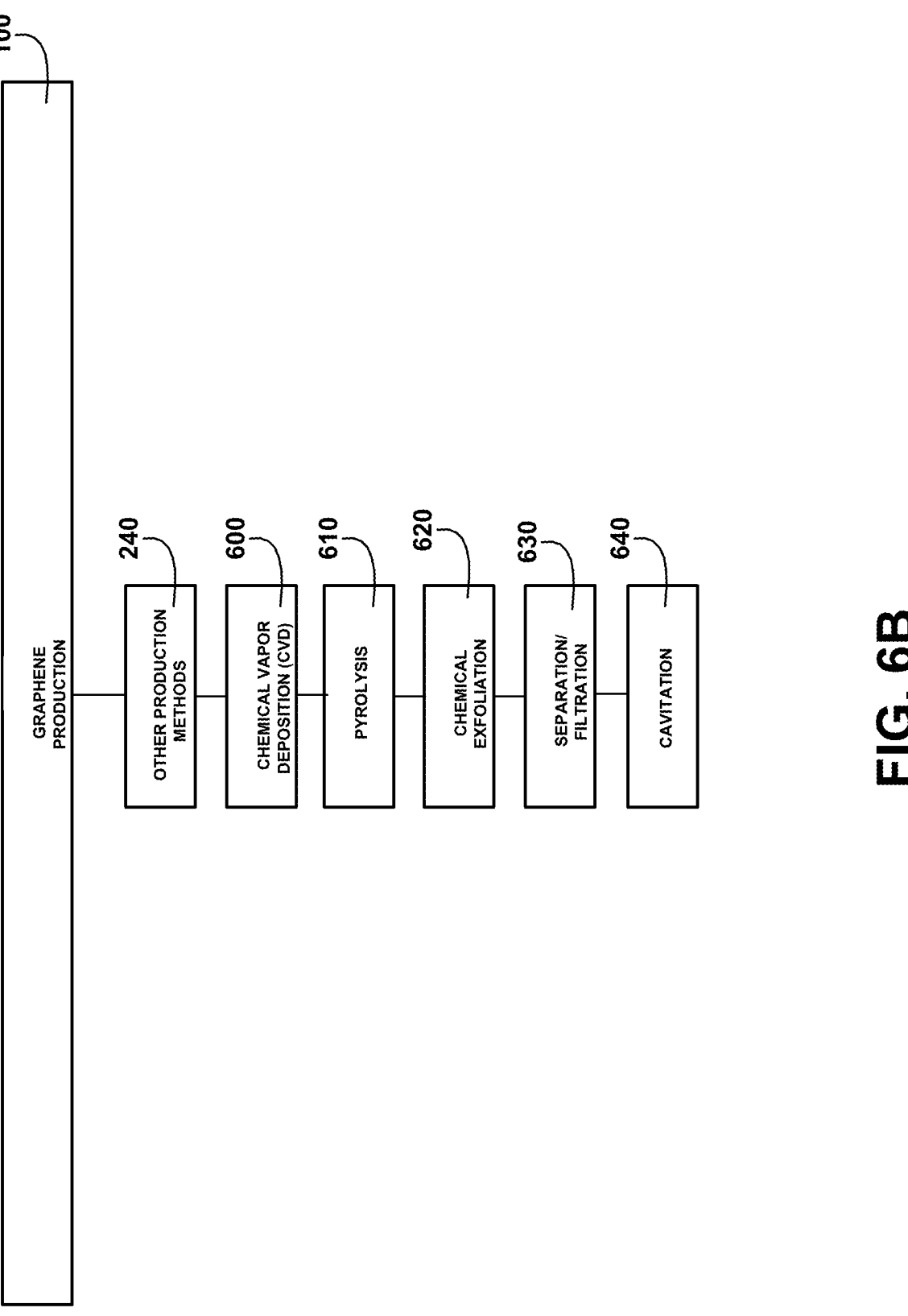
FIG. 6B shows a block diagram of an overview flow chart of a hierarchical diagram presenting alternative graphene production methods of one embodiment.

FIG. 6B shows a block diagram of an overview flow chart of a hierarchical diagram presenting alternative graphene production methods of one embodiment. FIG. 6B shows a hierarchical diagram presenting alternative graphene production 100 methods such as chemical vapor deposition (CVD) 600, pyrolysis 610, chemical exfoliation 620, separation/filtration 630, and cavitation 640. With reference to FIG. 6B, additional graphene production 100 methods are shown, representing alternative or supplementary synthesis pathways that may be employed individually or in combination with those described in FIG. 6A. These methods expand the toolkit for scalable and application-specific graphene manufacturing.

In one embodiment, chemical vapor deposition (CVD) 600 involves the catalytic decomposition of carbon precursors, such as methane or ethylene, at elevated temperatures onto metallic substrates (e.g., copper or nickel) to grow continuous monolayer or few-layer graphene films, and other production methods 240. This method yields highly crystalline graphene suitable for electronic applications.

Pyrolysis 610 entails the thermal decomposition of organic or polymeric carbon sources in an inert atmosphere, producing graphene-like carbon nanosheets with tunable morphology. This method is suited for bulk production and offers cost-efficiency for energy storage and composite applications.

Chemical exfoliation 620 includes oxidative treatments, such as modified methods, which introduce oxygenated functional groups into graphite to produce graphene oxide, which may subsequently be reduced to obtain reduced graphene oxide (rGO). This approach offers high functional group density for dispersion and composite integration.

Separation/filtration 630 techniques are applied post-synthesis to isolate graphene layers of defined thicknesses using membrane filtration, crossflow, or tangential flow setups. This enables scalable sorting of graphene by lateral dimension and number of layers.

Cavitation 640 based exfoliation leverages high-energy ultrasonic fields or hydrodynamic shear to induce bubble collapse and layer separation in liquid media. This physical technique can be integrated with other solvent-based methods to enhance exfoliation efficiency and yield. The methods shown in FIG. 6B may be combined with those in FIG. 6A or followed by purification, drying, and transfer processes as described above, to ensure graphene quality, stability, and compatibility with downstream functionalization and dispersion.

Figure 7A:
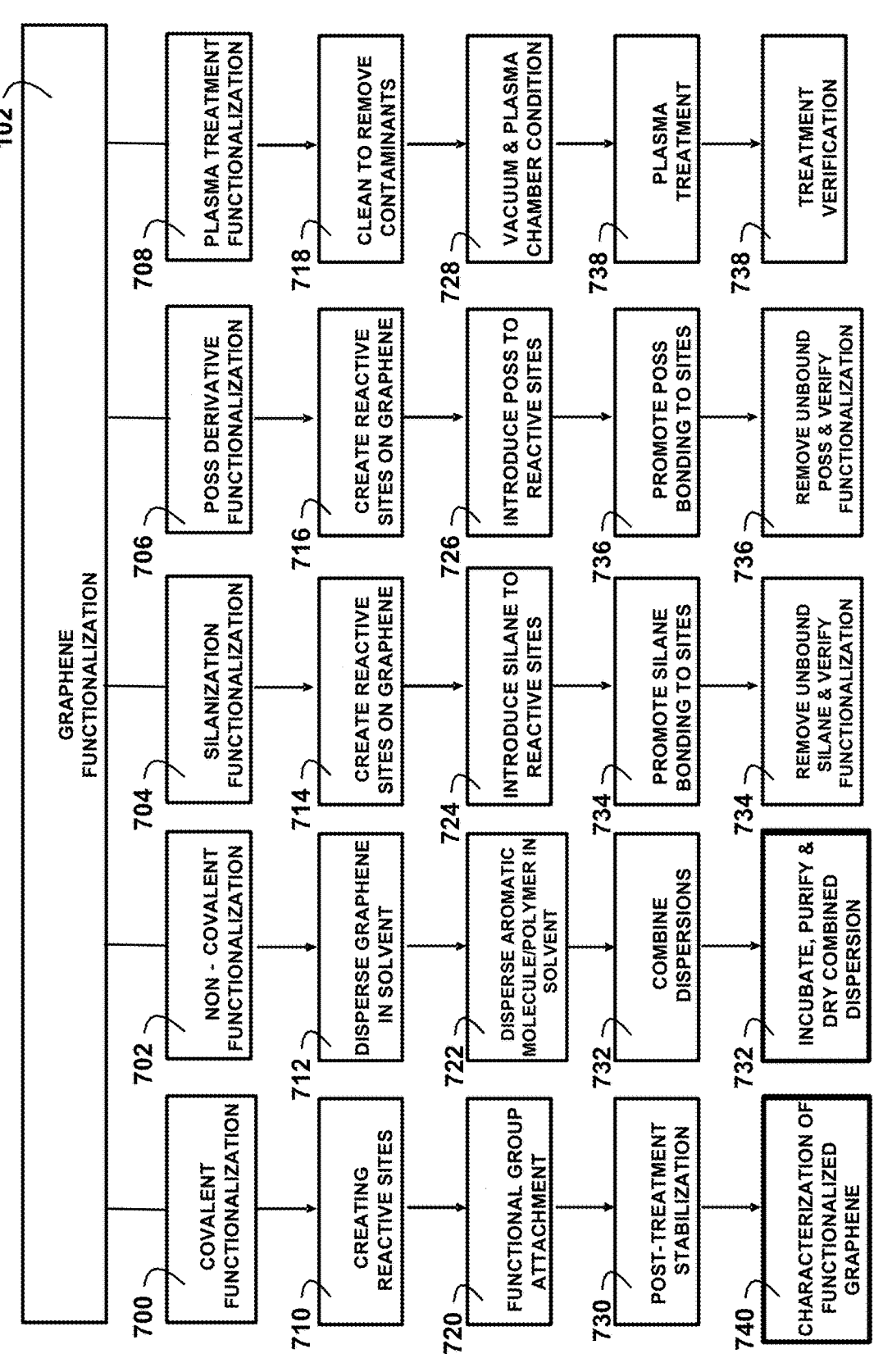
FIG. 7A shows a block diagram of an overview flow chart of sequential steps for graphene functionalization of one embodiment.

FIG. 7A shows a block diagram of an overview flow chart of sequential steps for graphene functionalization of one embodiment. FIG. 7A shows a flow diagram detailing sequential steps for graphene functionalization 102 via covalent functionalization 700, non-covalent 702, silanization 704, POSS 706, and plasma-based routes 708. With reference to FIG. 7A, the invention provides a set of complementary methods for graphene functionalization 102, each tailored to improve dispersion stability, enable biofunctionalization, or modify surface reactivity of graphene materials for downstream applications.

In one exemplary embodiment, covalent functionalization 700 includes a step of creating reactive sites 710 on the graphene surface via chemical oxidation, plasma exposure, or electrochemical activation. This is followed by a functional group attachment 720 using reactive intermediates such as diazonium salts, acyl chlorides, or carboxylic acids. A post-treatment stabilization 730 step ensures covalent bond retention and reduces re-oxidation. Final characterization of the functionalized graphene 740 is performed using techniques including XPS, FTIR, and Raman spectroscopy. In a particular embodiment, electrochemical pre-activation using mild anodic oxidation in 0.1 M $KNO_3$ (1.5 V vs Ag/AgCl) is used to enhance oxygen group density, improving functionalization efficiency by at least 20%.

In another embodiment, non-covalent functionalization 702 is accomplished by dispersing graphene in a solvent 712 and separately disperse an aromatic molecule/polymer in a compatible solvent 722.

These solutions are combined dispersions 732, and the mixture is incubated, purified, and dried combined dispersion 742 to yield a stable graphene dispersion 106 functionalized through IT-IT stacking, hydrophobic, or van der Waals interactions. In one preferred example, a temperature-gradient incubation protocol is employed, gradually lowering the temperature from 60° C. to 4° C. over a 4-hour period. This process improves molecular alignment and enhances surface coverage, as confirmed by Raman D/G band analysis and contact angle measurements.

In another exemplary embodiment, silanization functionalization 704 includes creating reactive sites on graphene 714, typically through oxidation or plasma pre-treatment, followed by introducing silane to reactive sites 724 bearing functional termini. These silane molecules promote silane bonding to sites 734 via hydrolysis-condensation reactions, and unreacted material is processed to remove unbound silane and verify functionalization 744. Silanization allows for subsequent covalent or non-covalent attachment of probes, polymers, or biological ligands.

In another embodiment, POSS derivative functionalization 706 follows a similar process. A process to create reactive sites on graphene 716, and POSS molecules are processed to introduce POSS to reactive sites 726. The bonding process is to promote POSS bonding to sites 736 using thermal activation or solvent polarity gradients, and unbound POSS is processed to remove unbound POSS and verify functionalization 746 of surface coverage. In one particular embodiment, a sequential solvent exchange process is used, beginning with a polar solvent such as DMSO or ethanol, and transitioning to a low-polarity solvent like toluene or terpineol before POSS addition. This approach enhances interfacial compatibility and improves Si 2p XPS signal and wettability.

In another embodiment, plasma treatment functionalization 708 includes surface cleaning to clean to remove contaminants 718, vacuum and plasma chamber condition 728, and plasma treatment 738 using ionized gases such as $O_2$, $N_2$, or $NH_3$. A final treatment verification 748 step includes surface energy, XPS, and contact angle measurements. In a preferred approach, a dual-gas plasma sequence is used: oxygen plasma introduces oxygen containing functional groups such as carboxyl and hydroxyl groups, and subsequent ammonia plasma introduces amino groups for bifunctional surface modification. Functional group incorporation is confirmed via O 1s and N 1s XPS spectra.

Figure 7B:
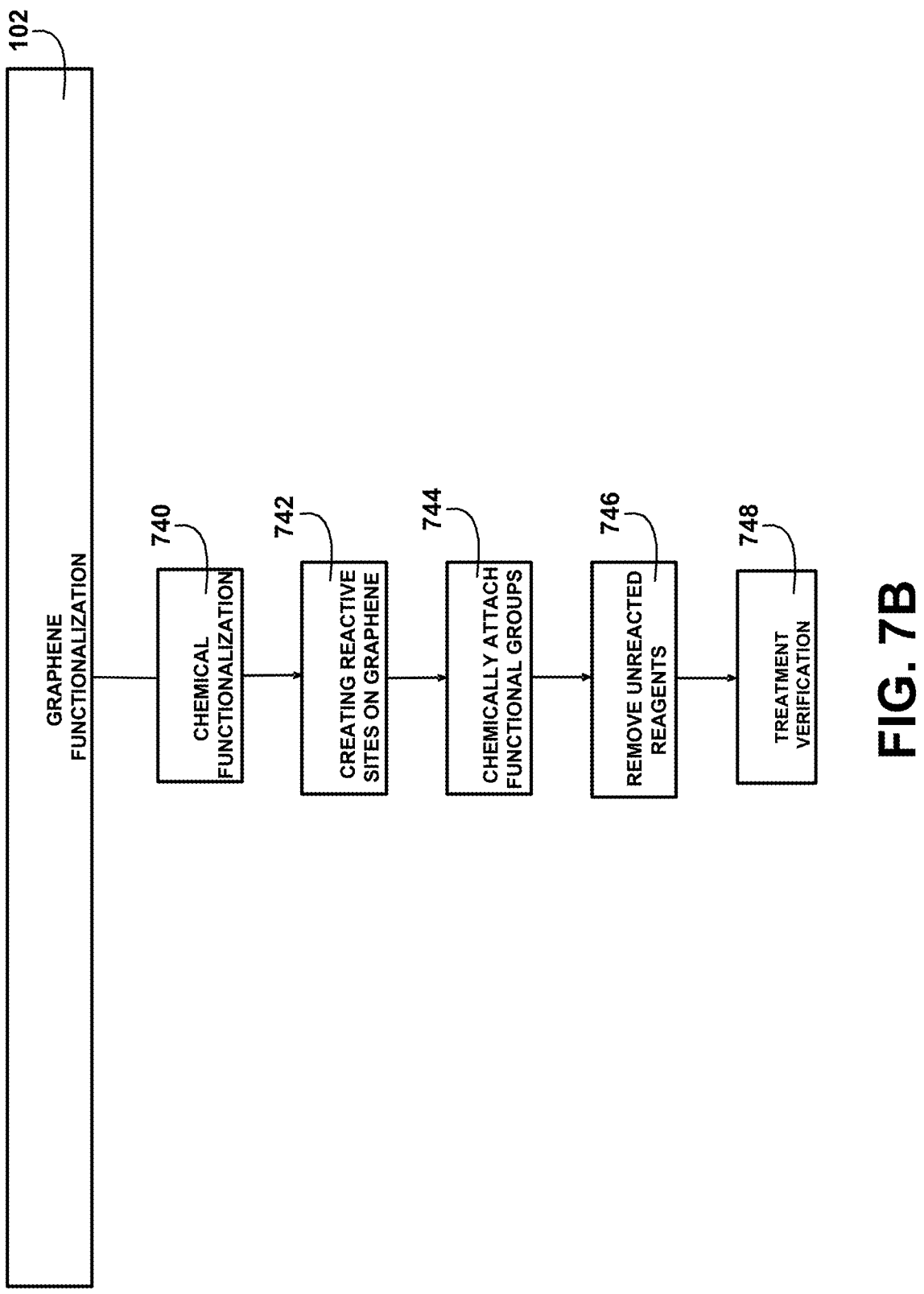
FIG. 7B shows a block diagram of an overview flow chart of sequential chemical functionalization steps of one embodiment.

FIG. 7B shows a block diagram of an overview flow chart of sequential chemical functionalization steps of one embodiment. FIG. 7B shows in a graphene functionalization 102 a flow diagram showing sequential chemical functionalization 740 steps including reactive site creation, chemically attach functional groups 744 and verification. With reference to FIG. 7B, an exemplary chemical functionalization pathway is disclosed. The process begins by creating reactive sites on graphene 742, using oxidants, diazonium intermediates, or halogenation reactions to introduce sites suitable for covalent bonding.

Next, specific functional groups are chemically attached to the reactive sites using well-controlled solution-phase reactions under ambient or elevated temperatures. Functional groups may include ester, ether, carbonyl carboxyl, amine, sulfonate, or alkyl chains depending on the application.

After functionalization, the material is treated to remove unreacted reagents 746 using washing, dialysis, or vacuum drying techniques. A final treatment verification 748 step is performed using elemental and chemical analysis methods such as XPS, TGA, or spectroscopic profiling to confirm surface modification.

Figure 8A:
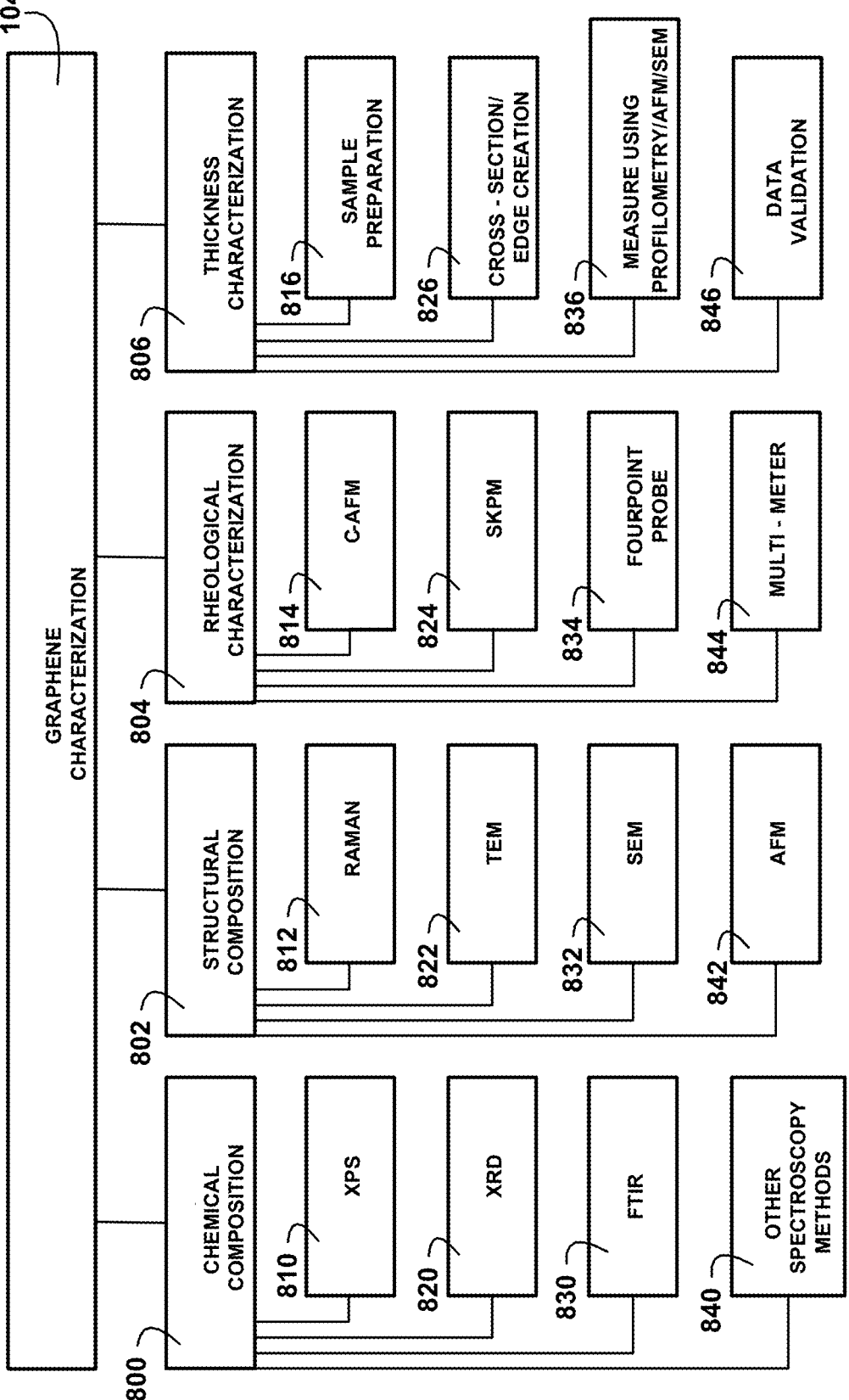
FIG. 8A shows a block diagram of an overview of a hierarchical diagram listing instrumentation methods of one embodiment.
Figure 8B:
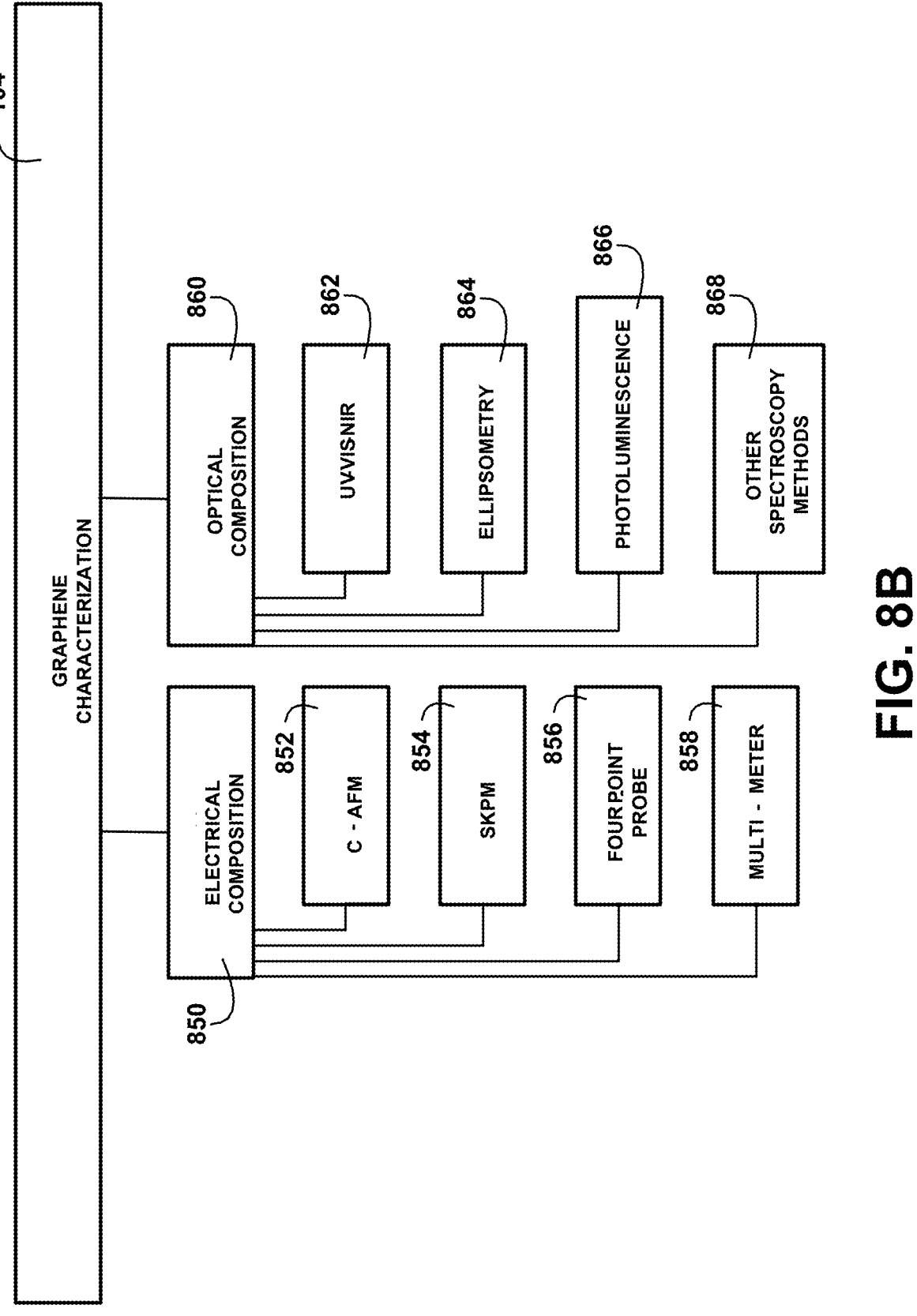
FIG. 8B shows a block diagram of an overview of a hierarchical diagram listing methods for electrical and optical characterization of one embodiment.

In one exemplary embodiment, the chemical functionalization involves the use of aryl diazonium salts, where graphene is treated with 4-nitrophenyl diazonium under acidic conditions to introduce nitrophenyl groups. Verification includes increased D/G Raman ratio and a decrease in contact angle from >90° to <60°, indicating improved hydrophilicity. With reference to FIGS. 8A and 8B, the invention provides a comprehensive suite of graphene characterization 104 methods used to validate the chemical, structural, electrical, optical, rheological, and thickness properties of graphene materials post-synthesis and functionalization.

FIG. 8A shows a block diagram of an overview of a hierarchical diagram listing instrumentation methods of one embodiment. FIG. 8A shows a hierarchical diagram listing instrumentation methods used for chemical, structural, rheological, and thickness of graphene characterization 104.

Chemical composition 800 analysis includes XPS 810, XRD 820, FTIR 830, and other spectroscopy methods 840. These techniques evaluate elemental content, bonding states, and surface chemistry. Samples are typically vacuum-annealed to remove contaminants. XPS is used for functional group quantification via peak deconvolution, XRD for crystallinity, and FTIR (in ATR mode) for surface functional groups. Additional methods may include EDS, SIMS, or AES for nanoscale mapping.

Structural composition 802 is characterized via Raman 812 spectroscopy, TEM 822, SEM 832, and AFM 842. Raman 812 identifies defects and strain; TEM 822 provides lattice resolution; SEM 832 offers surface morphology; and AFM 842 enables nanoscale topography. Clean imaging is supported by UHV or cryo-prep protocols.

Rheological characterization 804 and electrical properties are assessed through C-AFM 814, SKPM 824, four-point probe 834, and multi-meter 844 analysis. These methods provide local and bulk measurements of conductivity, surface potential, and sheet resistance. C-AFM 814 and SKPM 824 offer nanometer-resolution data, while four-point probe 834 and multi-meter 844 methods are used for device-scale validation.

Thickness characterization 806 involves sample preparation 816, edge or cross-section creation 826, measure using profilometry, AFM, or SEM 836, and data validation 843. These steps ensure a reliable quantification of graphene layer count and film uniformity.

FIG. 8B shows a block diagram of an overview of a hierarchical diagram listing methods for electrical and optical characterization of one embodiment. FIG. 8B shows a hierarchical diagram listing methods for electrical and optical characterization of graphene characterization 104 materials. Some of the methods for electrical characterization includes electrical composition 850, C-AFM 852, SKPM 854, four-point probe 856, and multi-meter 858.

Optical composition 860 is evaluated by UV-VIS-NIR 862, ellipsometry 864, photoluminescence (PL) 866, and other spectroscopy techniques 868. These characterize transmittance, optical constants, bandgap, and emission. PL is particularly useful for graphene oxide or defect-state analysis, while ellipsometry supports in situ monitoring of film modification. With reference to FIG. 1, and in greater detail to FIG. 5 and FIGS. 9A-9B, the invention encompasses dispersion systems and ink compositions comprising functionalized graphene nanoflakes.

FIG. 9A shows a block diagram of an overview of a hierarchical diagram organizing graphene dispersion components of one embodiment. FIG. 9A shows a hierarchical diagram organizing graphene dispersion 106 components by type, including organic solvents 500, non-organic solvents 510, surfactants 520, and POSS derivatives 530.

These systems enable formulation of printable or sprayable materials for sensors, flexible electronics, and coatings. The dispersion media are categorized into six classes: organic solvents 500, non-organic solvents 510, surfactants, 520, POSS derivatives 530, silane coupling agents 540 and aqueous mediums 550 of FIG. 5. Each category is subdivided into groups tailored to improve dispersion quality, ink rheology, chemical stability, and substrate adhesion.

In one embodiment, the dispersion medium comprises an organic solvent 500 selected from: polar aprotic solvents 910, alcohol-based solvents 920, glycol ethers and ether-modified alcohols 930, esters and lactates 940, or terpene-modified or aromatic hydrocarbons 950. These solvents enhance exfoliation efficiency, stabilize graphene through polarity or steric hindrance and improve thermal compatibility with flexible substrates.

Polar aprotic solvents 910 are particularly useful for dispersing nanomaterials such as graphene due to their high dielectric constants, good solvating ability for polymers and surface groups and ability to stabilize dispersed graphene without donating protons. Exemplary polar aprotic solvents 910 include 1,3-dimethyl-2-imidazolidinone (DMI), 1,4-dioxane, acetonitrile (MeCN), dimethyl sulfoxide (DMSO), dimethylacetamide (DMAc), dimethylformamide (DMF), diethylene glycol dimethyl ether (diglyme), ethylene carbonate (EC), γ-butyrolactone (GBL), N-methyl-2-pyrrolidone (NMP), propylene carbonate (PC), sulfolane, tetrahydrofuran (THF), triethylene glycol dimethyl ether (triglyme), and triethylene glycol monomethyl ether.

Alcohol-based solvents 920 are effective in dispersing functionalized graphene due to their moderate polarity, hydrogen bonding capabilities, and compatibility with both hydrophilic and partially hydrophobic surfaces. These solvents can aid in exfoliation, reduce agglomeration through steric and hydrogen bond interactions, and serve as co-solvents in hybrid systems with surfactants 520 or polymers. Exemplary alcohol-based solvents 920 include ethanol, isopropanol, n-butanol, tert-butanol, 2-ethylhexanol, benzyl alcohol, cyclohexanol, glycerol, and ethylene glycol. These solvents are particularly useful for preparing aqueous-organic inks, promoting wetting on polar substrates, and supporting biocompatible or green formulation strategies.

Glycol ethers and ether-modified alcohols 930 offer a unique balance of polarity, boiling point, and hydrogen bonding capacity, making them particularly advantageous for stabilizing graphene in hybrid polymer matrices. Their ether functionalities reduce hydrogen bond donation while maintaining strong solvation of polar surface groups, aiding in the uniform dispersion of graphene flakes. Moreover, their tunable volatility and low toxicity make them suitable for aqueous-compatible inks and slow-evaporation film formulations. Exemplary solvents include diethylene glycol monoethyl ether (Carbitol), triethylene glycol monomethyl ether, propylene glycol monomethyl ether acetate (PGMEA), and ethylene glycol butyl ether (Butyl Cellosolve). These solvents enable precise control over drying profiles and promote interfacial adhesion when co-formulated with polymers such as PVP, polyacrylates, cellulose derivatives or polyurethane dispersions.

Esters and lactates 940 are biodegradable solvents that support high loading of functionalized graphene while facilitating compatibility with ester-functional polymers and waterborne systems. Their mild solvating power promotes controlled swelling of polymer chains without inducing graphene agglomeration. Esters such as ethyl lactate, butyl acetate, and methyl propionate can be used to fine-tune the rheology and evaporation rate of printable inks. Exemplary esters include butyl acetate, ethyl acetate, isopropyl acetate, methyl acetate, propyl acetate, methyl propionate, ethyl propionate, isobutyl acetate, isobutyl isobutyrate, diethyl malonate, methyl benzoate, butyl benzoate, dimethyl phthalate, and diethyl succinate, while exemplary lactates include ethyl lactate, butyl lactate, methyl lactate, isopropyl lactate, and benzyl lactate. These solvents are particularly useful in green chemistry applications, allowing dispersion of graphene into resins or coatings without the need for aggressive surfactants 520 or co-solvent systems.

Terpene-modified and aromatic hydrocarbons 950 such as terpineol, dipentene, and limonene oxide are advantageous for dispersing graphene into resin-rich formulations due to their ability to interface with both hydrophobic $sp^2$ domains and functionalized edges. These solvents provide extended wetting time, reduce foam generation during mixing, and offer natural compatibility with phenolic resins, alkyds, and other hydrophobic polymer backbones. Their aromatic structure also facilitates IT-IT interactions with graphene surfaces, improving flake alignment and dispersion uniformity in applications such as flexible electronics and thermal adhesives. Exemplary terpene-modified and aromatic hydrocarbons 950 include α-terpineol, dipentene, limonene oxide, p-cymene, dihydromyrcenol, methyl naphthalene, 1-methylnaphthalene, cumene, styrene, and isopropylbenzene.

Non-organic solvents 510 are particularly valuable for dispersing functionalized graphene in systems where organic solvent contamination must be minimized or where thermal and dielectric stability are critical. These include five subcategories:

Ionic liquids 912 are non-volatile, thermally stable salts that exist in the liquid phase at or near room temperature. Their tunable cation-anion combinations allow tailored surface energy and polarity, enabling efficient dispersion of both oxidized and pristine graphene. Exemplary ionic liquids 912 include 1-ethyl-3-methylimidazolium tetrafluoroborate (EMIM-BF$_4$), 1-butyl-3-methylimidazolium hexafluorophosphate (BMIM-PF$_6$), and choline-based deep eutectic solvents (DES).

Polar inorganic solvents 922 include water-compatible, non-carbon-based solvents such as phosphoric acid, sulfuric acid, or concentrated nitric acid. These solvents are particularly effective for oxidative exfoliation or dispersing graphene oxides. They offer strong hydrogen bonding and high dielectric properties, allowing for stabilization of ionizable surface groups on graphene flakes.

Supercritical fluids 932 especially supercritical carbon dioxide (scCO$_2$)—provide an environmentally friendly, residue-free dispersion medium. Supercritical fluids 932 exhibit gas-like diffusivity and liquid-like solvating power, ideal for tuning dispersion behavior via pressure and temperature control. Functionalized graphene can be treated in scCO$_2$ systems with or without co-solvents to produce dry, agglomeration-resistant powders.

Waters 942 represents purified or deionized water used as the sole dispersion medium or in combination with stabilizers. These systems are often used in green, biocompatible, or bioanalytical applications, especially when combined with surfactants 520 or biopolymers.

Other non-organic solvents 952 encompass any remaining mineral, inorganic salt solutions, or reactive oxide-based solvents used in niche processing strategies. These include zinc chloride hydrate melts, lithium salt slurries, or molten borates. Such systems are typically used in high-temperature exfoliation, functionalization, or electrochemical intercalation-based graphene preparation and dispersion. Together, these non-organic solvents 510 offer alternatives to conventional organic media, expanding the application of graphene dispersions 106 into environmentally constrained, high-temperature, or chemically robust systems, including battery slurries, flame-retardant composites, and catalytic inks.

Surfactants 520 of FIG. 5 are utilized in graphene dispersion 106 formulations to provide steric and electrostatic stabilization of graphene nanoflakes. Surfactant subclasses include non-ionic 914 surfactants 520, anionic 924 surfactants 520, cationic 934 surfactants 520, and other surfactants 944. Non-ionic 914 surfactants such as Pluronic® block copolymers, Tween® 20/80, and Triton X-100 adsorb onto graphene surfaces without altering charge, making them ideal for pH-independent stabilization. Anionic 924 surfactants, including sodium dodecyl sulfate (SDS) and sodium cholate, impart strong surface charge for dispersion in aqueous systems. Cationic 934 surfactants such as cetyltrimethylammonium bromide (CTAB) promote electrostatic stabilization under acidic conditions and facilitate deposition onto negatively charged substrates. Other surfactants 944 may include zwitterionic or fluorinated surfactants tailored for low-surface-energy substrates and solvent compatibility. Surfactant blends may be selected based on micelle formation, critical micelle concentration (CMC), and solvent-phase compatibility for printable ink systems.

POSS derivatives 530 are used to sterically and chemically stabilize functionalized graphene dispersions 106. Classes of these hybrid inorganic-organic modifiers include functional POSS 916, non-functional POSS 926, hybrid POSS 936, fluorinated POSS 946, and other POSS 956 variants. Functional POSS 916 molecules may include epoxy, glycidyl, amino, acrylate, and phenyl-functionalized cages such as Glycidyl Phenyl POSS and Phenyl PEG POSS. Hybrid POSS 936 derivatives like PEG-Phenyl POSS enhance dispersibility via both IT-IT interaction and hydrogen bonding. Fluorinated POSS 946 improves compatibility with fluoropolymers and hydrophobic matrices, and non-functional POSS 926 provides physical flake separation without chemical reactivity. POSS additives are often pre-dispersed in a solvent such as ethanol, tetrahydrofuran (THF), or dimethylformamide (DMF) prior to incorporation into the graphene system. Novel aspects include the co-use of POSS and silanes in single-phase dispersions to modulate both edge and basal plane reactivity.

Figure 9B:
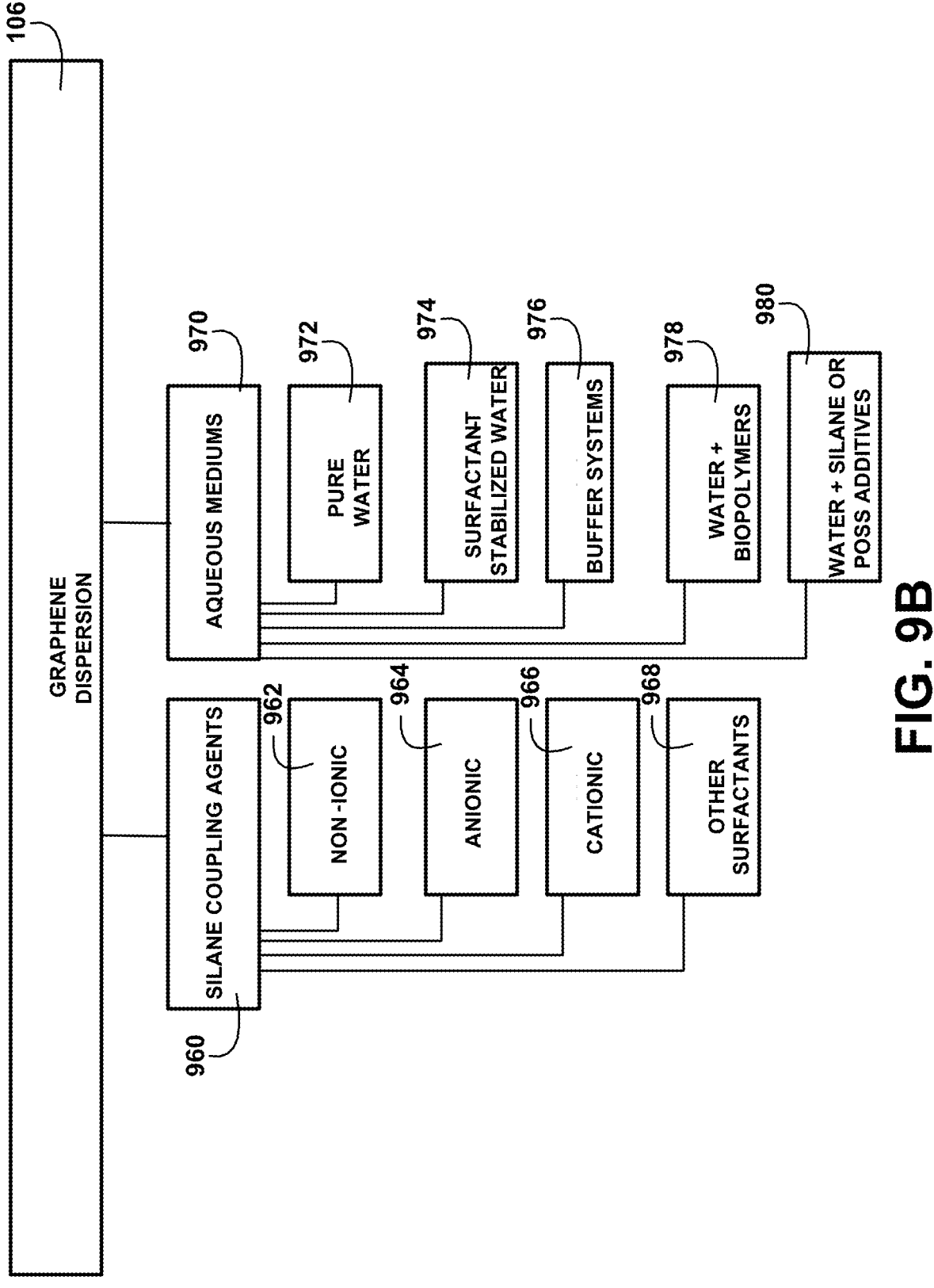
FIG. 9B shows a block diagram of an overview of a hierarchical diagram detailing the classification of silane coupling agents of one embodiment.

FIG. 9B shows a block diagram of an overview of a hierarchical diagram detailing the classification of silane coupling agents of one embodiment. FIG. 9B shows a hierarchical diagram detailing the classification of silane coupling agents 540 and aqueous dispersion systems for graphene dispersion 106.

Silane coupling agents 540 are used to chemically anchor functionalized graphene to polymer matrices or substrates. Subcategories include non-ionic 914, anionic 924, cationic 934, and other surfactants 944. Exemplary silanes include 3-aminopropyltriethoxysilane (APTES), 3-glycidyloxypropyltrimethoxysilane (GPTMS), and fluorosilanes like perfluorooctyltriethoxysilane. These molecules form covalent bonds with oxide or hydroxyl groups on substrates while interacting with graphene via van der Waals forces or covalent coupling. Silanes may be dispersed in ethanol, isopropanol, or water-alcohol mixtures, and deposition may be preceded by plasma or oxidative treatment of the graphene surface. In some embodiments, silanes are used in conjunction with POSS additives to create orthogonal surface functionality for multi-domain hybrid adhesion.

Aqueous mediums 550 represent environmentally friendly dispersion platforms for functionalized graphene and are categorized as pure water 972, surfactant-stabilized water 974, buffer systems 976, water with biopolymers 978, and water containing silane or POSS additives 980. Pure water systems are often used for highly oxidized graphene oxide and exhibit colloidal stability without surfactants. Surfactant-stabilized water systems employ SDS, SDBS, or PEG-based agents to prevent flake aggregation.

Buffer systems, such as phosphate-buffered saline (PBS), provide pH stabilization to maintain consistent dispersion behavior during storage or processing. Biopolymer-containing systems include gelatin, chitosan, or cellulose derivatives to impart shear stability, biodegradability, and film-forming capability. Additives such as silanes or POSS may be introduced into aqueous systems to functionalize graphene in situ or modulate dispersion charge density and hydrophobicity, enabling hybrid aqueous-organic interface engineering.

In one non-limiting formulation, a dispersion contains 10% w/v graphene flakes stabilized in a THF-PVP matrix with added hybrid POSS 936 and non-ionic 914 surfactants. This composition exhibits viscosity and surface tension suitable for inkjet or screen printing, and provides sheet resistances below 50Ω/sq after thermal curing at 120° C. Other ink systems include combinations of silanes and terpene-based solvents or water-borne POSS for adhesion to PET, Kapton®, glass, ceramic, or silicon. The functionalized graphene material described herein exhibits co-optimized surface chemistry and structural integrity, as shown in FIGS. 10A and 10B.

Figures 10A, 10B:
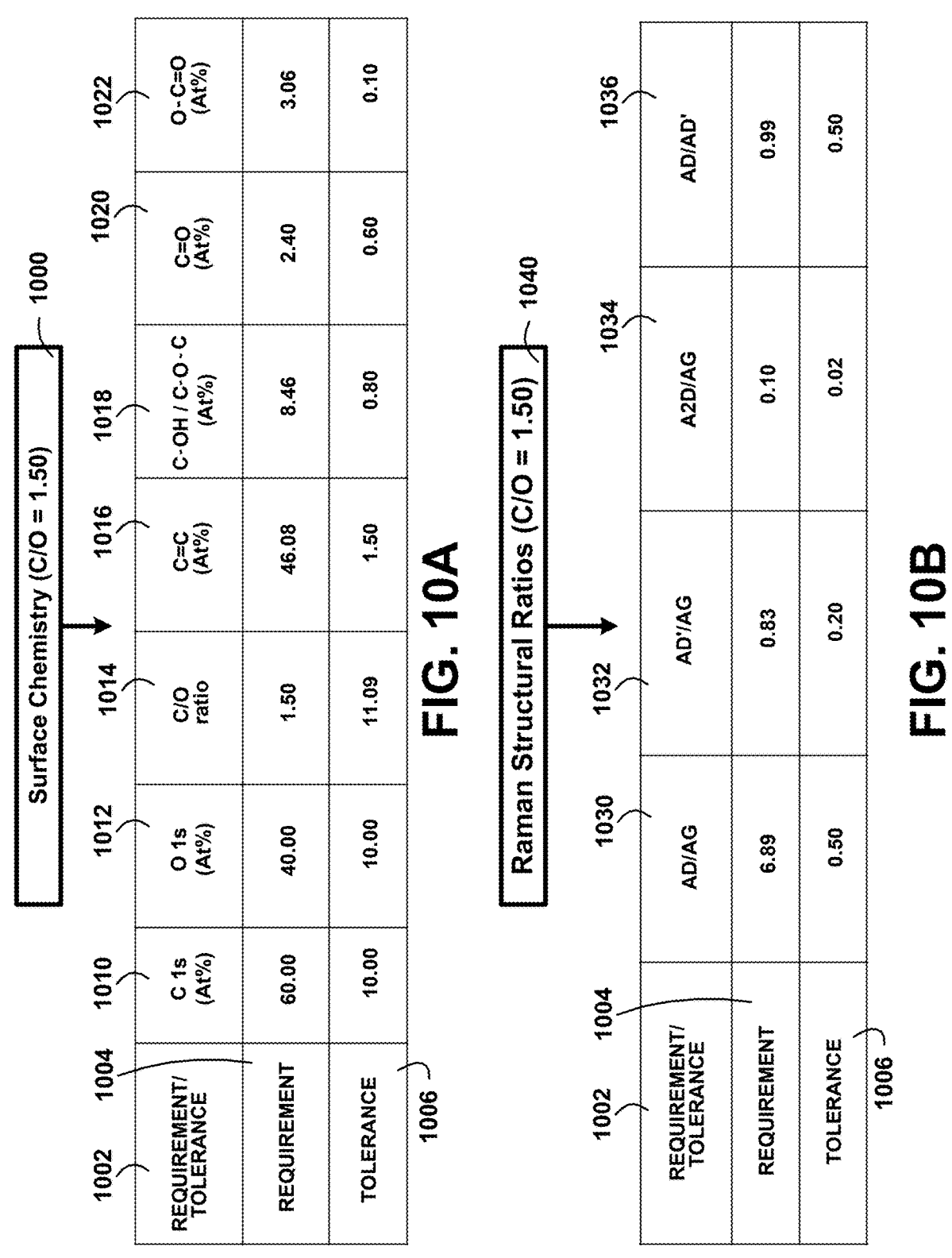
FIG. 10A shows a block diagram of an overview of a data table presenting surface chemistry specifications for graphene at a carbon-to-oxygen (C/O) ratio of 1.50 of one embodiment.
FIG. 10B shows a block diagram of an overview of a data table presenting Raman spectroscopic structural ratios for the sample shown in FIG. 10A of one embodiment.

FIG. 10A shows a block diagram of an overview of a data table presenting surface chemistry specifications for graphene at a carbon-to-oxygen (C/O) ratio of 1.50 of one embodiment. FIG. 10A shows a data table presenting surface chemistry specifications for graphene at a carbon-to-oxygen (C/O) ratio of 1.50, as measured by X-ray photoelectron spectroscopy (XPS). C═C (sp$^2$ carbon) domains enable strong TT-TT stacking with the aromatic DNA bases, anchoring the probe via planar interactions. Hydroxyl (C—OH) and carbonyl (C═O) groups enhance surface polarity and hydrogen bonding capacity, improving probe orientation and aqueous stability. Carboxyl (O—C═O) and ether (C—O—C) groups modulate surface charge and dispersibility, influencing adsorption strength and minimizing nonspecific aggregation.

FIG. 10A Surface Chemistry (C/O=1.50) 1000 showing REQUIREMENT/TOLERANCE 1002, REQUIREMENT 1004 and TOLERANCE 1006 for results for C 1s (At %) 1010, O 1s (At %) 1012, C/O ratio 1014, C═C(At %) 1016, C—OH/C—O—C(At %) 1018, C═O (At %) 1020, and O—C═O (At %) 1022.

X-ray photoelectron spectroscopy (XPS) reveals a carbon-to-oxygen (C/O) atomic ratio of 1.50±11.09, comprising 60.00±10.00 atomic percent carbon (C 1s) and 40.00±10.00 atomic percent oxygen (O 1s). The C 1s spectrum is deconvoluted to yield 46.08±1.50 atomic percent sp$^2$ carbon (C=C), 8.46±0.80 atomic percent hydroxyl and ether groups (C—OH/C—O—C), 2.40±0.60 atomic percent carbonyl (C=O), and 3.06±0.10 atomic percent carboxyl or ester (O—C=O).

FIG. 10B shows a block diagram of an overview of a data table presenting Raman spectroscopic structural ratios for the sample shown in FIG. 10A of one embodiment. FIG. 10B shows a data table presenting Raman spectroscopic structural ratios. FIG. 10B Raman Structural Ratios (C/O=1.50) 1050 showing Requirement/Tolerance 1002, Requirement 1004, And Tolerance 1006 for results for AD/AG 1030, AD'/AG 1032, A2D/AG 1034, and AD/AD' 1036.

Raman spectroscopy further confirms structural features, including a D-to-G band area ratio (A(D)/A(G)) of 6.89±0.50, a D'-to-G ratio (A(D')/A(G)) of 0.83±0.20, a 2D-to-G ratio (A (2D)/A(G)) of 0.10±0.02, and a D-to-D' ratio (A(D)/A(D')) of 0.99±0.50. These values reflect a high density of edge defects, low graphitic stacking, and uniform defect symmetry, yielding specific surface areas between approximately 100 m$^2$/g and 1500 m$^2$/g. The resulting material offers a balance between surface functionalization and retained conjugation, supporting dispersion stability and semiconductive properties. This integrated specification enables precise control over both colloidal and electronic behavior, distinguishing the material from conventional graphene systems optimized for only one attribute.

Figures 11A, 11B:
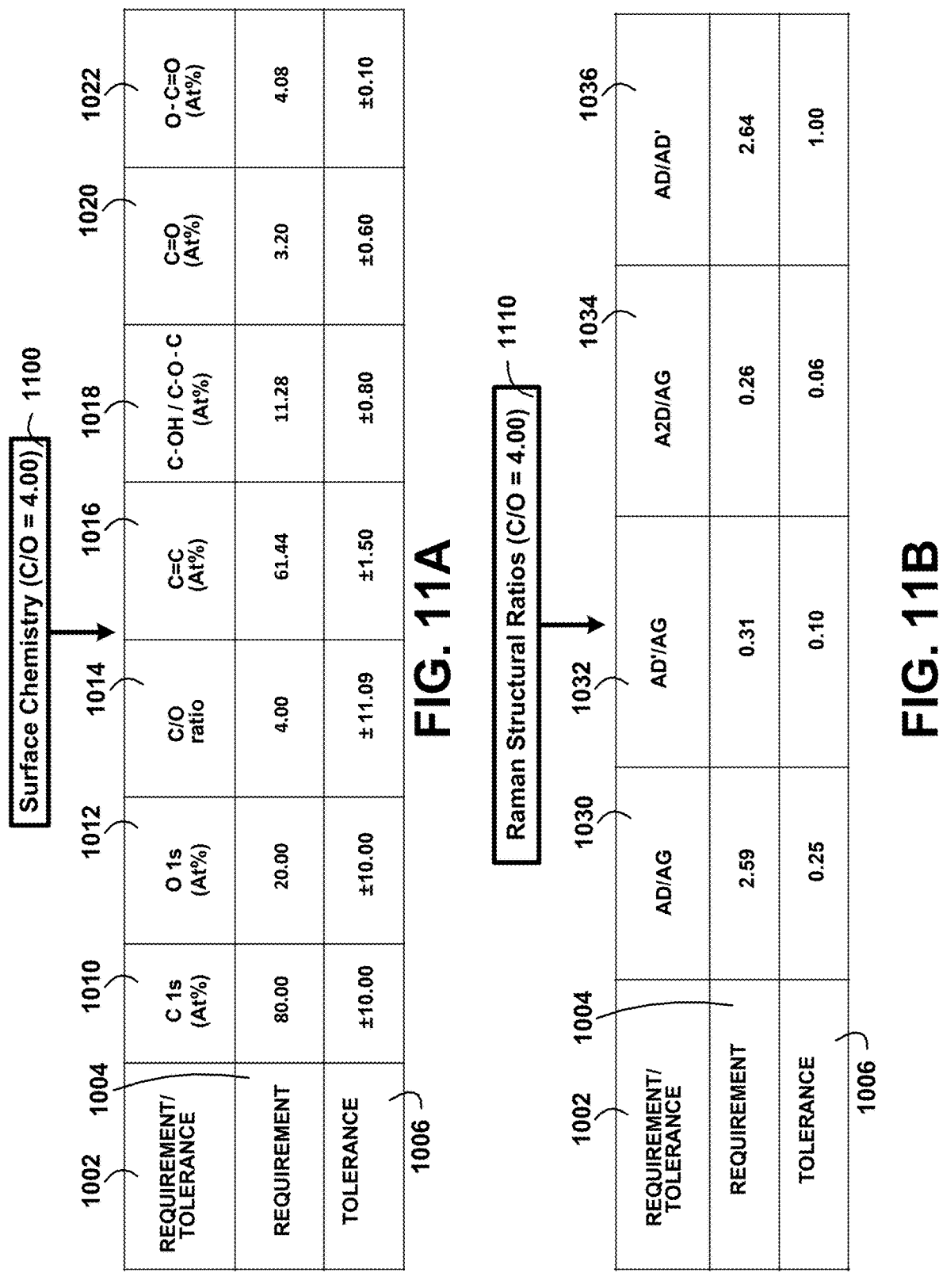
FIG. 11A shows a block diagram of an overview of a data table presenting XPS-based surface chemistry targets for graphene at a C/O ratio of 4.00 of one embodiment.
FIG. 11B shows a block diagram of an overview of a data table presenting Raman spectroscopic structural ratios for the sample shown in FIG. 11A of one embodiment.

With reference to FIGS. 11A and 11B, a graphene-based material is disclosed exhibiting a defined carbon-to-oxygen atomic ratio (C/O ratio) of 4.00±11.09, as determined by X-ray photoelectron spectroscopy (XPS). The elemental composition includes 80.00±10.00 atomic percent carbon (C 1s) and 20.00±10.00 atomic percent oxygen (O 1s). High-resolution deconvolution of the C 1s peak yields 61.44±1.50 atomic percent sp$^2$ carbon (C=C), 11.28±0.80 atomic percent hydroxyl and ether groups (C—OH/C—O—C), 3.20±0.60 atomic percent carbonyl (C=O), and 4.08±0.10 atomic percent carboxyl or ester groups (O—C=O), as shown in FIG. 11A.

FIG. 11A shows a block diagram of an overview of a data table presenting XPS-based surface chemistry targets for graphene at a C/O ratio of 4.00 of one embodiment. FIG. 11A shows Surface Chemistry (C/O=4.00) 1100 showing REQUIREMENT/TOLERANCE 1002, REQUIREMENT 1004, and TOLERANCE 1006 for results for C 1s (At %) 1010, O 1s (At %) 1012, C/O ratio 1014, C=C(At %) 1016, C—OH/C—O—C(At %) 1018, C=O (At %) 1020, and O—C=O (At %) 1022. These oxygen-containing functional groups play a critical role in the dispersion stability and chemical reactivity of the material.

FIG. 11B shows a block diagram of an overview of a data table presenting Raman spectroscopic structural ratios for the sample shown in FIG. 11A of one embodiment. FIG. 11B shows a data table showing Raman structural data for the sample in FIG. 11A. FIG. 11B Raman Structural Ratios (C/O=4.00) 1110 showing Requirement/Tolerance 1002, Requirement 1004, And Tolerance 1006 for results for AD/AG 1030, AD'/AG 1032, A2D/AG 1034, and AD/AD' 1036.

Complementary Raman spectroscopic analysis, shown in FIG. 11B, provides insight into lattice disorder and conjugation retention. Area-based peak integrations yield a D-to-G band area ratio (A(D)/A(G)) of 2.59±0.25, a D'-to-G ratio (A(D')/A(G)) of 0.31 ±0.10, a 2D-to-G ratio (A (2D)/A(G)) of 0.26±0.06, and a D-to-D' ratio (A(D)/A(D')) of 2.64±1.00. The A(D)/A(G) ratio reflects moderate edge and basal plane disorder, while the A(D')/A(G) and A (2D)/A(G) ratios provide metrics for stacking order, strain, and exfoliation extent.

A distinguishing feature of this material is the engineered balance between oxygen functional group content and Raman-active defect signatures. Unlike randomly oxidized graphene exhibiting amorphous disorder, the present formulation maintains structural continuity while providing chemically accessible sites. This co-optimization supports formulation of water-based inks, hybrid conductive films, and chemically modifiable interfaces. The defined tolerance ranges across both spectroscopic domains enable precision tuning of colloidal behavior and electronic properties for use in printed electronics, sensors, and functional coatings.

Figures 12A, 12B:
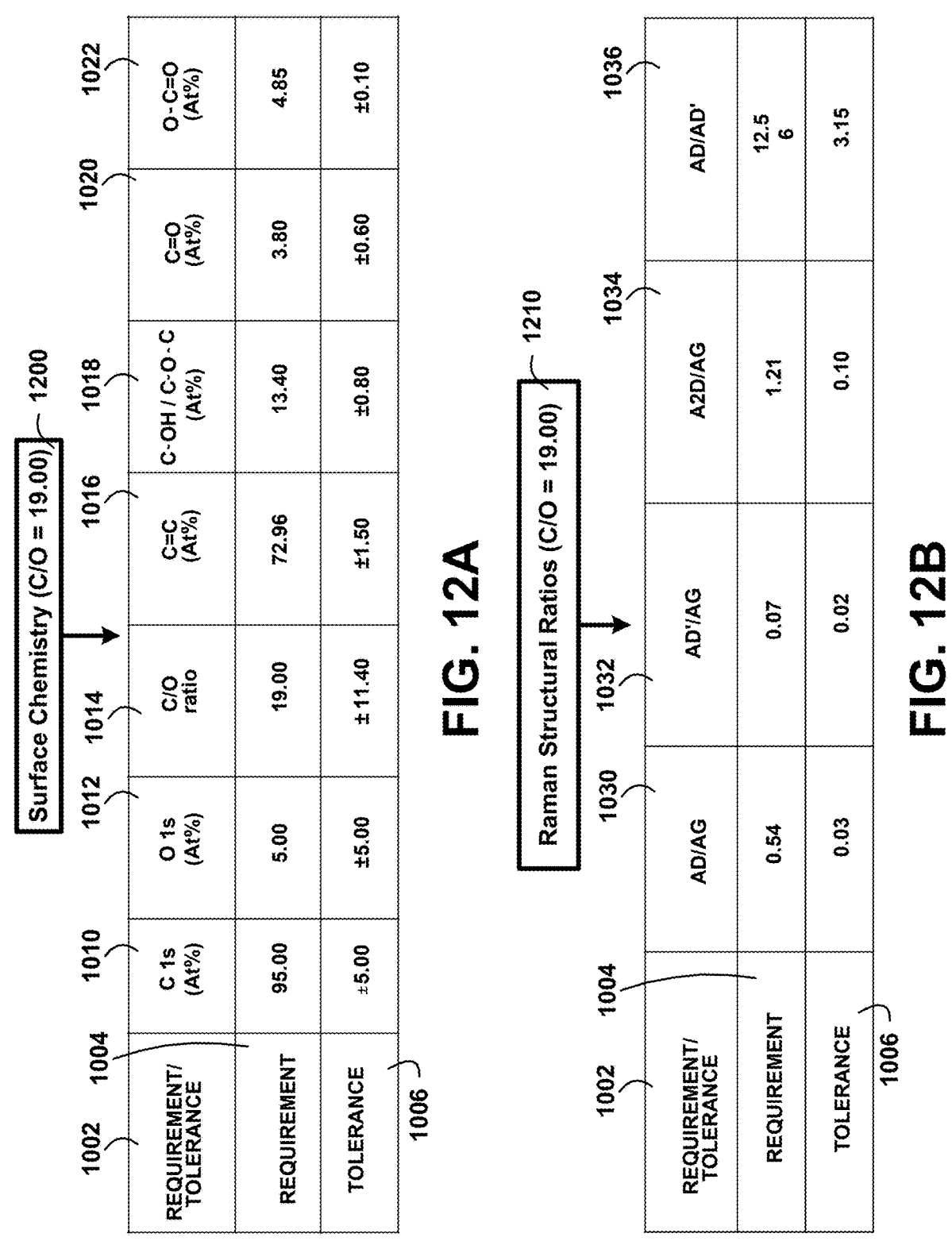
FIG. 12A shows a block diagram of an overview of a data table detailing surface chemistry targets for graphene at a C/O ratio of 19.00 of one embodiment.
FIG. 12B shows a block diagram of an overview of a data table presenting Raman spectroscopic structural ratios for the sample shown in FIG. 12A of one embodiment.

With reference to FIGS. 12A and 12B, a graphene-based material is disclosed having a defined carbon-to-oxygen atomic ratio (C/O ratio) of 19.00±11.40, as measured by X-ray photoelectron spectroscopy (XPS). The atomic composition includes 95.00±5.00 atomic percent carbon (C 1s) and 5.00±5.00 atomic percent oxygen (O 1s). The high-resolution C 1s spectrum is deconvoluted to quantify specific bonding environments, including 72.96±1.50 atomic percent sp$^2$ carbon (C=C), 13.40±0.80 atomic percent hydroxyl and ether groups (C—OH/C—O—C), 3.80±0.60 atomic percent carbonyl (C=O), and 4.85±0.10 atomic percent carboxyl or ester groups (O—C=O), as shown in FIG. 12A.

FIG. 12A shows a block diagram of an overview of a data table detailing surface chemistry targets for graphene at a C/O ratio of 19.00 of one embodiment. FIG. 12A shows a data table detailing surface chemistry targets for graphene at a C/O ratio of 19.00.

FIG. 12A Surface Chemistry (C/O=19.00) 1200 showing REQUIREMENT/TOLERANCE 1002, REQUIREMENT 1004, and TOLERANCE 1006 for results for C 1s (At %) 1010, O 1s (At %) 1012, C/O ratio 1014, C=C(At %) 1016, C—OH/C—O—C(At %) 1018, C=O (At %) 1020, O—C=O (At %) 1022.

In other exemplary formulations, atomic ratios of 90±5% C and 10±5% O may be achieved, with functional group contributions of approximately 70±5% sp$^2$ carbon, 10±5% hydroxyl/ether, 5±5% carbonyl, and 5±5% carboxyl, enabling tunability across oxygen content windows.

FIG. 12B shows a block diagram of an overview of a data table presenting Raman spectroscopic structural ratios for the sample shown in FIG. 12A of one embodiment. FIG. 12B shows a data table presenting Raman structural metrics for the material shown in FIG. 12A. FIG. 12B shows a data table presenting Raman structural metrics for the material shown in FIG. 12A. Requirement/Tolerance 1002, Requirement 1004, And Tolerance 1006 for results for AD/AG 1030, AD'/AG 1032, A2D/AG 1034, and AD/AD' 1036.

Raman spectroscopy, as shown in FIG. 12B, confirms structural order via area-based band integration. The D-to-G band area ratio (A(D)/A(G)) is 0.54±0.03, the D'-to-G ratio (A(D')/A(G)) is 0.07±0.02, the 2D-to-G ratio (A (2D)/A(G)) is 1.21±0.10, and the D-to-D' ratio (A(D)/A(D')) is 12.56±3.15. These values indicate minimal Raman-detectable disorder, preserved conjugation, and consistent lattice ordering, with corresponding surface areas typically between about 100 m$^2$/g and 1500 m$^2$/g.

A distinguishing feature of the disclosed material is the co-optimization of high sp$^2$ carbon content and selective, low-level oxygen incorporation, producing a semi-pristine lattice structure with targeted functional group reactivity. The correlation between low A(D)/A(G) and A(D')/A(G) ratios and the dominant $sp^2$ carbon framework results in a material that retains both high electrical performance and surface modification capability. This formulation is particularly suited for transparent conductive films, bioactive sensor substrates, and printed electronic coatings where low defect density and controlled surface polarity are critical. The ability to precisely position the material within a defined structure-chemistry performance envelope represents a novel advancement over conventional reduced or randomly oxidized graphene.

Figures 13A, 13B:
FIG. 13A shows a block diagram of an overview of a data table showing surface chemistry for near-pristine graphene with a C/O ratio of 99.00 of one embodiment.
FIG. 13B shows a block diagram of an overview of a data table summarizing Raman ratios for the material in FIG. 13A of one embodiment.

With reference to FIGS. 13A and 13B, a graphene-based material is presented having a carbon-to-oxygen atomic ratio (C/O ratio) of 99.00±1.09, corresponding to 99.00±2.00 atomic percent carbon (C 1s) and 1.00±2.00 atomic percent oxygen (O 1s), as measured by X-ray photoelectron spectroscopy (XPS). The deconvoluted C 1s spectrum shown in FIG. 13A reveals 76.03±1.50 atomic percent $sp^2$ carbon (C=C), 13.93±0.80 atomic percent hydroxyl and ether groups (C—OH/C—O—C), 3.96±0.60 atomic percent carbonyl (C=O), and 5.05±0.10 atomic percent carboxyl or ester groups (O—C=O), indicating extremely low oxidation while retaining a chemically addressable surface.

FIG. 13A shows a block diagram of an overview of a data table showing surface chemistry for near-pristine graphene with a C/O ratio of 99.00 of one embodiment. FIG. 13A shows Surface Chemistry (C/O=99.00) 1300, REQUIRE-MENT/TOLERANCE 1002, REQUIREMENT 1004, and TOLERANCE 1006 for results for C 1s (At %) 1010, O 1s (At %) 1012, C/O ratio 1014, C=C(At %) 1016, C—OH/C—O—C(At %) 1018, C=O (At %) 1020, O—C=O (At %) 1022.

FIG. 13B shows a block diagram of an overview of a data table summarizing Raman ratios for the material in FIG. 13A of one embodiment. FIG. 13B shows a data table summarizing Raman ratios for the material in FIG. 13A, indicating minimal defect content. The data table for FIG. 13B Raman Structural Ratios (C/O=99.00) 1310 showing Requirement/Tolerance 1002, Requirement 1004, And Tolerance 1006 for results for AD/AG 1030, AD'/AG 1032, A2D/AG 1034, and AD/AD' 1036.

Raman spectral characterization, as shown in FIG. 13B, yields a D-to-G band area ratio (A(D)/A(G)) of 0.03±0.01, a D'-to-G ratio (A(D')/A(G)) of 0.005±0.005, and a 2D-to-G ratio (A (2D)/A(G)) of 2.50±0.50. These spectral signatures are indicative of a near-pristine graphene lattice with minimal disorder and dominant 2D-band intensity, consistent with monolayer or few-layer graphene and high crystallinity. The A(D)/A(G) and A(D')/A(G) values confirm the absence of significant lattice defects, while the elevated A (2D)/A(G) reflects extended TT-conjugation and well-aligned graphitic domains.

A distinguishing feature of the disclosed material is the integration of an ultra-high $sp^2$ carbon framework with only trace oxygen incorporation, enabling a unique balance between electrical conductivity and functionalizability. In contrast to moderately oxidized formulations, the FIG. 13 composition exhibits exceptional purity and lattice preservation. This structural and chemical profile supports use in transparent conductive electrodes, high-frequency electronics, and optoelectronic applications where Raman activity, minimal defect content, and chemical stability are essential. The synergistic control of XPS-defined oxidation and Raman-defined structural coherence makes this material well suited for photonic, sensing, and energy conversion platforms demanding both performance and structural precision.

Figure 14:
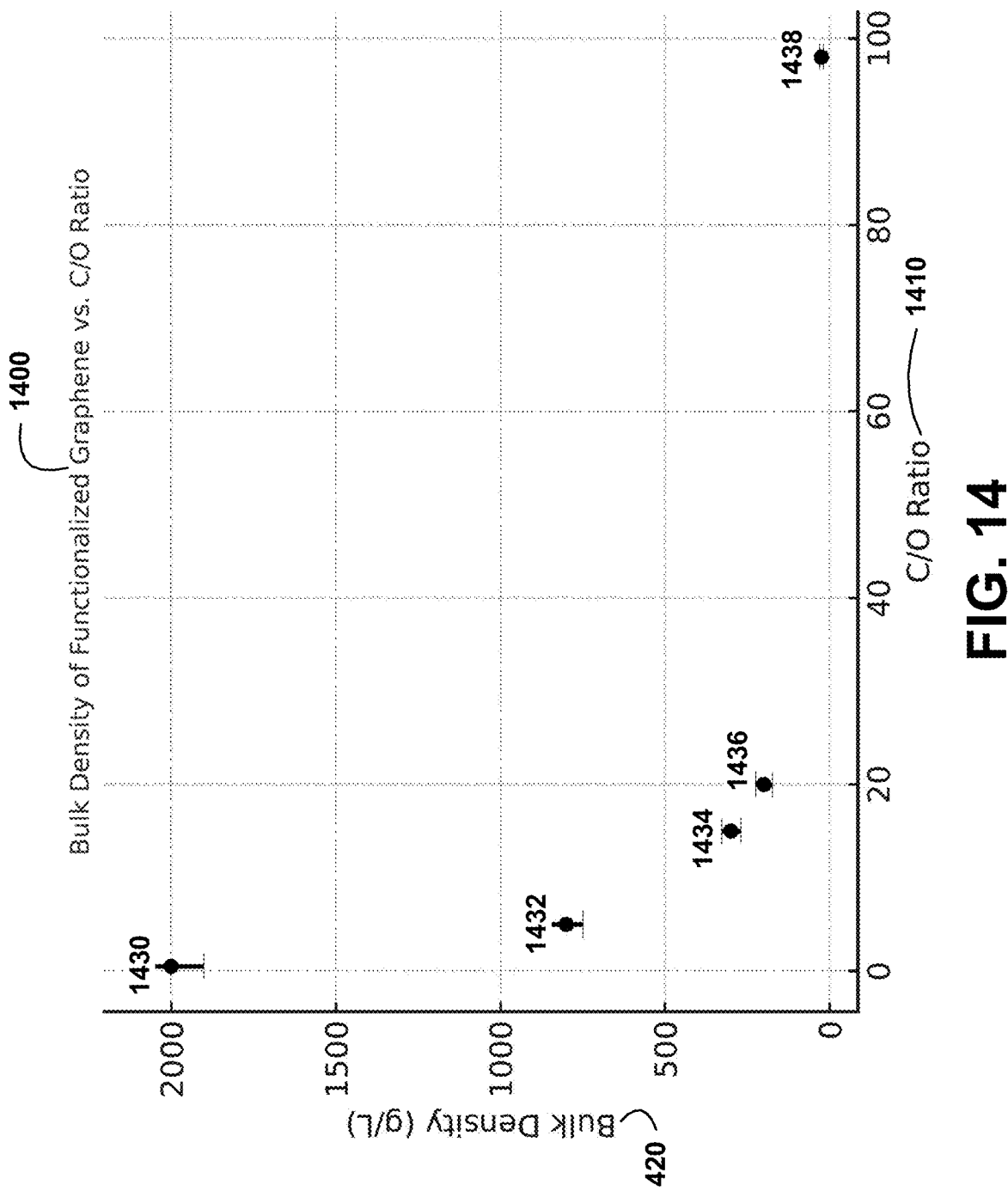
FIG. 14 shows a block diagram of an overview of a hybrid diagram of an inverse correlation of one embodiment.

FIG. 14 shows a block diagram of an overview of a hybrid diagram of an inverse correlation of one embodiment. FIG. 14 shows a hybrid diagram (data plot with hierarchical annotations) illustrating the inverse correlation between C/O ratio and bulk density of graphene samples, with each point labeled by structural class.

Referring now to FIG. 14, the relationship between carbon-to-oxygen atomic ratio (C/O ratio 1410) and bulk density of functionalized graphene materials is illustrated as the bulk density of functionalized graphene vs. C/O ratio 1400. As shown, the material exhibits a strong inverse correlation between C/O ratio and bulk density (g/L) 1420. At a C/O ratio of approximately 1.50 (reference numeral 1430), the bulk density reaches 1994 g/L±150 g/L, indicative of a highly oxidized, compacted structure with high functional group content and associated interlayer interactions. As the C/O ratio increases, the density systematically decreases: to 749 g/L±100 g/L at a C/O of 4.00 (reference 1432), 296 g/L±50 g/L at a C/O of 13.79 (reference 1434), 238 g/L±40 g/L at a C/O of 19.00 (reference 1436), and as low as 30 g/L±10 g/L at a C/O of 99.00 (reference 1438).

These trends reflect the progressive removal of oxygen-containing functional groups and the restoration of extended $sp^2$ domains, reducing mass per volume as stacking, hydration, and cross-sheet interactions diminish. The intermediate density range of 238-296 g/L (1436, 1438) represents a tunable region wherein oxidation-induced defects and conjugated domain continuity are balanced to enable both chemical functionality and structural ordering.

This engineered correlation between surface oxidation level and bulk material density supports formulation of graphene-based materials for diverse applications such as lightweight composites, tunable-thickness coatings, and processable reactive films. The ability to select a target C/O ratio and achieve a corresponding material density within controlled tolerances enhances both the performance flexibility and manufacturing scalability of functionalized graphene systems.

Figure 15:
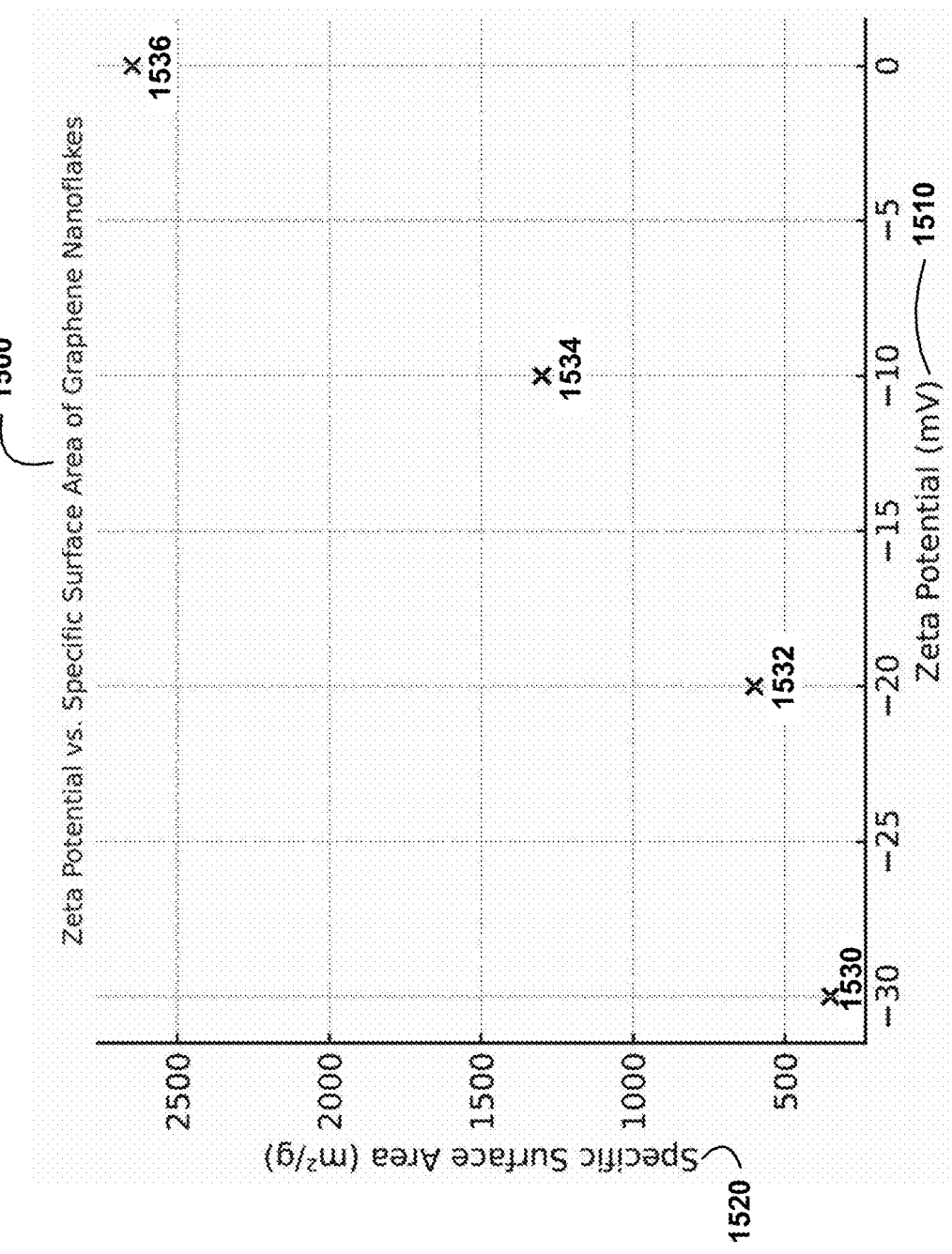
FIG. 15 shows a block diagram of an overview of a scatter plot with categorical annotations of one embodiment.

FIG. 15 shows a block diagram of an overview of a scatter plot with categorical annotations of one embodiment. FIG. 15 shows a hybrid diagram (scatter plot with categorical annotations) illustrating the relationship between zeta potential and specific surface area (SSA) of graphene, with each point annotated by degree of functionalization and crystallinity.

With reference to FIG. 15, a correlation is illustrated between Zeta Potential vs. Specific Surface Area (SSA) in functionalized graphene nanoflakes 1500. This figure demonstrates how electrostatic surface charge, quantified by zeta potential, correlates with underlying material structure, including crystallinity, flake stacking order, and the degree of chemical functionalization. Each data point is annotated with a reference numeral for clarity. The data point labeled 1536 corresponds to pristine or minimally functionalized graphene with non-detectable chemical modification, Bernal stacking, and 100% crystallinity.

This sample exhibits a near-neutral zeta potential of 0 mV and an SSA ($m^2$/g) 1520 of approximately 2630 $m^2$/g, reflecting an ordered lattice structure with minimal defect sites and high conjugation. As moderate edge functionalization is introduced (reference 1534), the zeta potential (mV) 1510 becomes more negative, approximately −10 mV, and crystallinity is reduced to ~75%. The flake stacking shifts from Bernal to partially disordered (stacked), and the SSA decreases to about 1315 m²/g. These changes reflect the initiation of oxygen group attachment and corresponding surface charge buildup.

Further chemical treatment and disordering (reference 1532) results in a zeta potential of roughly –20 mV, indicative of turbostratic stacking and ~50% crystallinity. The SSA at this stage drops to approximately 657.5 m²/g, corresponding to increased interlayer separation and partial loss of graphitic alignment. The most heavily functionalized graphene sample (reference 1530) exhibits a zeta potential near –30 mV and an SSA of approximately 328.75 m²/g. This condition is associated with twisted flake orientation, low crystallinity (~25%), and extensive surface modification via grafted chemical groups, resulting in maximal electrostatic repulsion and minimal in-plane order.

This data set demonstrates that zeta potential can serve as a functional proxy for evaluating graphene structure, oxidation state, and dispersion behavior. The observed trend provides a practical, scalable metric to infer interfacial reactivity and colloidal stability in aqueous or polar solvent systems, thereby guiding formulation choices for inks, coatings, and bio-interactive materials.

Figure 16:
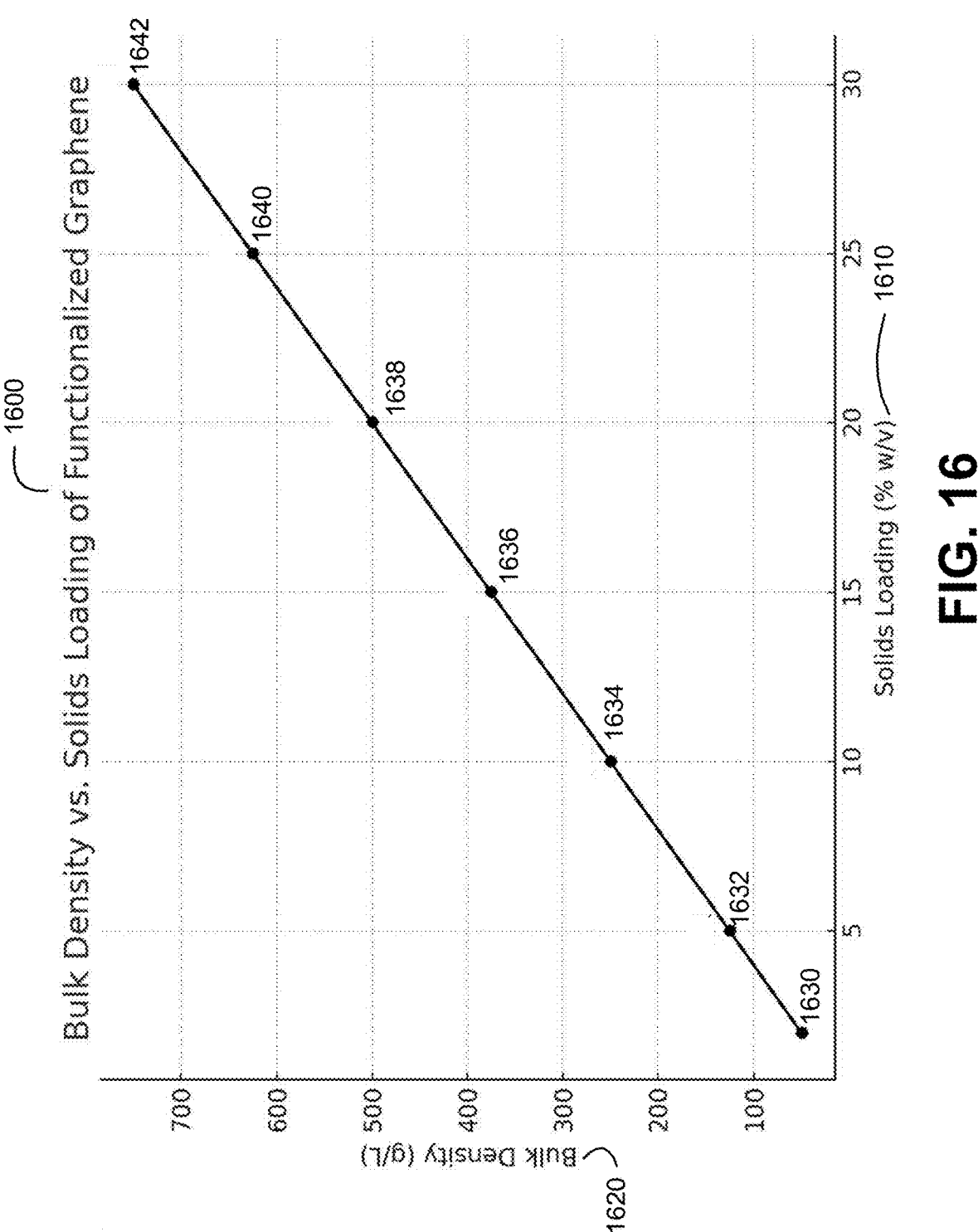
FIG. 16 shows a block diagram of an overview of functionalized graphene formulations of one embodiment.

FIG. 16 shows a block diagram of an overview of functionalized graphene formulations of one embodiment. FIG. 16 shows the estimated relationship between solids loading and bulk density in functionalized graphene formulations 1600. As shown, bulk density (g/L) 1620 increases linearly with solids concentration over the range of 2% to 30% w/v. At a solids loading (% w/v) 1610 of 2% w/v, the bulk density is approximately 50 g/L 1630; at 5% w/v, the bulk density is about 125 g/L 1632; and at 10% w/v, it reaches approximately 250 g/L 1634. Intermediate loadings include 15% w/v with a density of about 375 g/L 1636, 20% w/v at approximately 500 g/L 1638, and 25% w/v at 625 g/L 1640. At the upper end, a 30% w/v loading corresponds to a bulk density of about 750 g/L 1642. These values provide practical guidance for tuning dispersion concentration in ink, coating, and composite systems. The trend reflects how increasing flake content enhances packing efficiency and volumetric density, which are critical for adjusting viscosity, film thickness, and mass-loading in printable or castable formulations.

Figure 17:
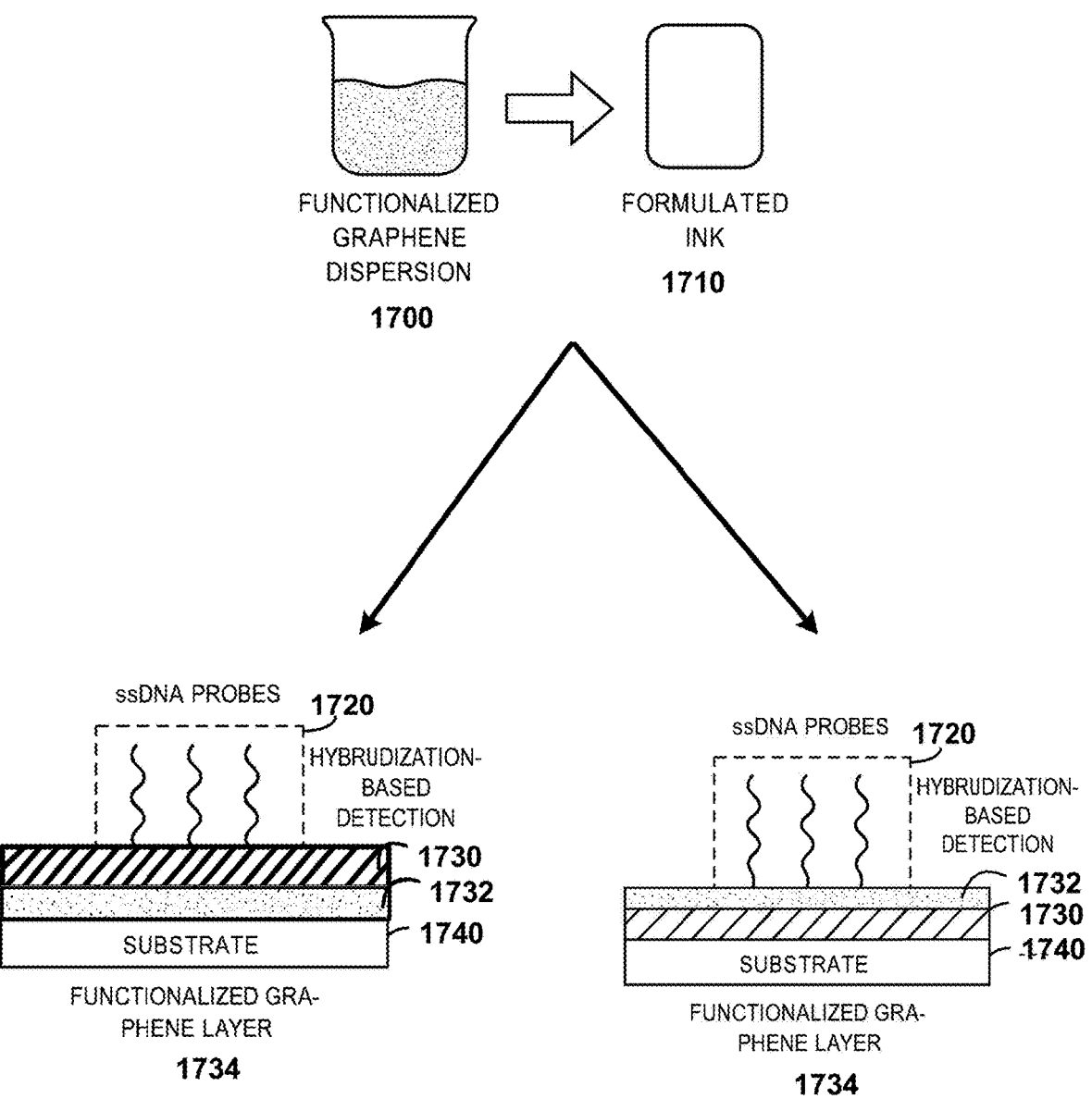
FIG. 17 shows for illustrative purposes only an example of a topmost functionalized graphene layer of one embodiment.

FIG. 17 shows for illustrative purposes only an example of a topmost functionalized graphene layer of one embodiment. FIG. 17 shows the stack-up includes a substrate 1740, an overlying conductive trace or patterned interconnect 1730, and a topmost functionalized graphene layer 1734. The compositions and dispersions described herein are suitable for a range of applications in printed electronics, biosensing, and coatings. In one exemplary embodiment, a screen-printable or inkjet-printable or spin coat-printable ink is formulated by dispersing functionalized graphene powder, exhibiting a carbon-to-oxygen (C/O) atomic ratio of about 19±11.40, into an functionalized graphene dispersion 1700, including at least one of glycols or terpineol, along with a steric stabilizing additive selected from polyhedral oligomeric silsesquioxane (POSS) derivatives and a binding polymer selected from a group of cellulose derivatives or vinyl polymer dispersions, at a concentration between about 2% w/v and about 30% w/v.

The resulting formulated ink 1710 is deposited onto a substrate 1740, which may comprise polyimide, glass, ceramic or polyethylene terephthalate (PET), to form a printed sensor region. As illustrated in FIG. 17, the stack-up includes a substrate 1740, an overlying conductive trace or patterned interconnect 1732, and a topmost functionalized graphene layer 1730. In another embodiment, the functionalized graphene layer 1730 may be printed directly onto the substrate 1740, followed by deposition of a conductive trace 1732 over the graphene layer, followed by biomolecule functionalization to form a bottom-contact configuration.

The functionalized graphene surface is chemically modified with oxygen-containing functional groups hydroxyl (C—OH), ether (C—O—C), carbonyl (C═O), carboxyl and ester (O—C═O) to enable immobilization of single-stranded DNA (ssDNA) probes 1714, facilitating hybridization-based detection 1720 of nucleic acids gene sequences indicative of cancer genes or pathogens, such as Influenza virus, Coronavirus, Respiratory Syncytial virus, Filovirus, Hepatitis C virus, *Staphylococcus aureus* bacteria or *Escherichia coli*. It should be appreciated that many types of biomolecules can be bound to the service of the graphene layer 1730, providing a very broad range of detection capabilities. This structure supports the fabrication of diagnostic biosensor platforms with tunable surface polarity, reproducible probe immobilization, and electronic signal response. Additional applications include transparent conductive films for touch sensors, flexible circuits, EMI shielding coatings, and field-deployable molecular diagnostics that maintain substrate adhesion and signal integrity without reliance on cold-chain logistics.

In certain embodiments, the functionalized graphene formulations disclosed herein are used in conjunction with molecular diagnostic platforms described in U.S. Patent Application Publication No. US20240081677A1, entitled "Molecular Detection Platforms and Hybridized Biosensors for Pathogen Screening," which is incorporated herein by reference in its entirety.

The foregoing has described the principles, embodiments, and modes of operation of the present invention. However, the invention should not be construed as being limited to the particular embodiments discussed. The above-described embodiments should be regarded as illustrative rather than restrictive, and it should be appreciated that variations may be made in those embodiments by workers skilled in the art without departing from the scope of the present invention as defined by the following claims.

What is claimed is:

1. A method of producing functionalized graphene powder, comprising:

creating few-layer graphene powder via at least one of energy-assisted, plasma, detonation, mechanical exfoliation, chemical exfoliation, thermal exfoliation, electrochemical processing, chemical vapor deposition (CVD), separation/filtration, pyrolysis and cavitation;

exposing the graphene powder to a functionalization process selected from at least one of covalent functionalization methods, non-covalent functionalization methods, silanization functionalization methods, POSS derivative functionalization methods, plasma treatment functionalization methods and chemical functionalization methods to introduce oxygen-containing functional groups and achieve a carbon-to-oxygen atomic ratio (C/O) of 19±11.40; and wherein the oxygen-containing functional groups are tuned to the following atomic percent (At %) targets and tolerances:

hydroxyl (C—OH) and ether (C—O—C) is 13.40±0.80 carbonyl (C═O) is 3.80±0.60 carboxyl and ester (O—C═O) is 4.85±0.10.

2. The method of producing functionalized graphene powder of claim 1, wherein the plasma treatment is performed at a pressure between 0.1 and 1 Torr, a temperature between 100° C. and 150° C., and a plasma power between 100 W and 300 W for a duration of 5,000 to 20,000 seconds using at least one gas selected from argon, oxygen, ammonia or atmospheric air.

3. The method of producing functionalized graphene powder of claim 1, further comprising performing sequential functionalization comprising POSS derivatives or silane treatment, wherein the resulting graphene powder demonstrates an increase in adhesion to polyimide, ceramic and glass substrates.

4. The method of producing functionalized graphene powder of claim 1, further comprising characterizing the powder by Raman spectroscopy to confirm an A(D)/A(G) ratio of about 0.54±0.03 and an A (2D)/A(G) ratio of about 1.21±0.10.

5. The method of producing functionalized graphene powder of claim 1, wherein the functionalized graphene powder is dispersed in at least one solvent selected from NMP, DMF, THF, glycols and terpineol and at least one steric stabilizing additive selected from polyhedral oligomeric silsesquioxane (POSS) derivatives.

6. The method of producing functionalized graphene powder of claim 5, wherein the graphene dispersion is combined at a concentration between about 2% w/v and about 30% w/v with at least one of a polymer dispersion selected from a group of polyurethane dispersions, acrylic emulsions, epoxy resins, cellulose-based polymer dispersions, vinyl polymer dispersions, or water-soluble film-formers to form printable or sprayable graphene inks.

7. The method of producing functionalized graphene powder of claim 6, wherein the printed or coated graphene material retains high electrical conductivity and tunable surface reactivity due to the controlled oxygen functionalization of the functionalized graphene powder.

8. A method for detecting a target nucleic acid in a biological sample, comprising:
    providing a biosensor comprising:
        a substrate;
        a conductive trace deposited on the substrate;
        a functionalized graphene layer deposited on the conductive trace, the functionalized graphene comprising oxygen-containing functional groups selected from hydroxyl (C—OH), ether (C—O—C), carbonyl (C=O), carboxyl and ester (O—C=O), and having a carbon-to-oxygen atomic ratio (C/O) of about 19±11.40; and
        single-stranded DNA (ssDNA) probes immobilized on the functionalized graphene layer;
    contacting the biosensor with a biological sample suspected of containing a complementary nucleic acid sequence; and
    detecting a change in electrical signal resulting from hybridization of the complementary nucleic acid sequence to the immobilized ssDNA probes.

9. The method of claim 8, wherein the change in electrical signal is measured by a change in resistance or direct current of the functionalized graphene layer.

10. The method of claim 8, wherein the target nucleic acid sequence is specific to a cancer gene sequence or a pathogen gene sequence selected from Influenza virus, Coronavirus, Respiratory Syncytial virus, Filovirus, Hepatitis C virus, *Staphylococcus aureus*, or *Escherichia coli*.

\*   \*   \*   \*   \*